United States Patent
Beuerlein et al.

(10) Patent No.: US 9,260,531 B2
(45) Date of Patent: Feb. 16, 2016

(54) ANTI-C-MET ANTIBODIES

(71) Applicant: Eli Lilly and Company, Indianapolis, IN (US)

(72) Inventors: Gregory Beuerlein, Spring Valley, CA (US); Julian Davies, La Jolla, CA (US); Irene Jennifer Denning, San Diego, CA (US); Ling Liu, Carmel, IN (US); Jirong Lu, Carmel, IN (US); Peter Edward Vaillancourt, Del Mar, CA (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 14/397,498

(22) PCT Filed: May 1, 2013

(86) PCT No.: PCT/US2013/039003
§ 371 (c)(1),
(2) Date: Oct. 28, 2014

(87) PCT Pub. No.: WO2013/169532
PCT Pub. Date: Nov. 14, 2013

(65) Prior Publication Data
US 2015/0118238 A1    Apr. 30, 2015

Related U.S. Application Data

(60) Provisional application No. 61/778,806, filed on Mar. 13, 2013, provisional application No. 61/644,591, filed on May 9, 2012.

(51) Int. Cl.
| | |
|---|---|
| *C07K 16/32* | (2006.01) |
| *A61K 39/395* | (2006.01) |
| *G01N 33/574* | (2006.01) |
| *C07K 16/28* | (2006.01) |
| *A61K 39/00* | (2006.01) |

(52) U.S. Cl.
CPC ............. *C07K 16/32* (2013.01); *C07K 16/2863* (2013.01); *G01N 33/5748* (2013.01); *A61K 2039/505* (2013.01); *C07K 2317/565* (2013.01); *C07K 2317/92* (2013.01); *G01N 2333/71* (2013.01); *G01N 2333/82* (2013.01); *G01N 2800/52* (2013.01)

(58) Field of Classification Search
CPC .......................................... C07K 16/00–16/468
See application file for complete search history.

(56) References Cited

U.S. PATENT DOCUMENTS

| | | | | |
|---|---|---|---|---|
| 8,030,302 B2* | 10/2011 | Li | ........................ | C07D 401/12 |
| | | | | 514/232.5 |
| 8,217,148 B2* | 7/2012 | Davies | ............... | C07K 16/2863 |
| | | | | 530/387.1 |
| 8,268,836 B2* | 9/2012 | Wu | ....................... | C07D 487/04 |
| | | | | 514/259.31 |
| 8,398,974 B2* | 3/2013 | Davies | ............... | C07K 16/2863 |
| | | | | 424/130.1 |
| 2003/0017979 A1 | 1/2003 | Mack et al. | | |
| 2011/0129459 A1 | 6/2011 | Kuramochi et al. | | |
| 2011/0319597 A1 | 12/2011 | Simpson et al. | | |
| 2012/0034232 A1 | 2/2012 | Gauthier et al. | | |
| 2014/0349310 A1* | 11/2014 | Davies | ............... | C07K 16/2863 |
| | | | | 435/7.4 |

FOREIGN PATENT DOCUMENTS

WO    WO 2011/0020925 A1    2/2011

* cited by examiner

*Primary Examiner* — Sheela J Huff
*Assistant Examiner* — Jessica H Roark
(74) *Attorney, Agent, or Firm* — Robert B. Johnson

(57) ABSTRACT

The present invention relates to antibodies, or antigen-binding fragments thereof, that bind to the extracellular domain of human c-Met, compositions and kits comprising such c-Met antibodies, or antigen-binding fragments thereof, and methods of using the same for detection of human c-Met that aid in identifying patients with tumors expressing or overexpressing human Met and/or improving their treatment response with anti-c-Met therapeutics.

24 Claims, No Drawings

ANTI-C-MET ANTIBODIES

The present invention relates to the field of medicine. More particularly, the present invention relates to antibodies, or antigen-binding fragments thereof, that bind human c-Met (also known as MET) to form a detectable c-Met/anti-c-Met antibody complex useful in diagnostic techniques that require labeling, marking, or identifying human c-Met, such as imaging, prognostic or predictive applications that aid in identifying patients with tumors expressing or overexpressing human c-Met protein and/or improving their treatment response with anti-c-Met therapeutics.

The protein c-Met is a member of the receptor tyrosine kinase superfamily, and the receptor for hepatocyte growth factor (HGF), also known as scatter factor (SF). The mature human c-Met protein is composed of a completely extracellular alpha subunit, a beta subunit comprised of an extracellular ligand binding domain, a single transmembrane domain, and a cytoplasmic tyrosine kinase domain.

Activation of human c-Met by HGF has been shown to enhance characteristics that are associated with an invasive cell phenotype: proliferation, migration, morphogenesis, survival, and protease synthesis. The human c-Met signaling pathway is one of the most frequently dysregulated pathways in human cancers, and is implicated in virtually all types of solid tumors. The stimulation, overexpression, or mutation of human c-Met is observed in many types of cancers, including colon, breast, ovary, lung, liver, prostate, pancreas, bile ducts, brain, thyroid, kidney, gastric, as well as melanomas and sarcomas. These biochemical and genetic abnormalities of the HGF/c-Met signaling axis are correlated with poor clinical outcomes and drug resistance in cancer patients.

Due to the role of the human c-Met signaling pathway in regulating initial steps of tumor formation and subsequent disease dissemination, human c-Met is considered to be an attractive target for cancer therapy with small molecule and antibody antagonists of HGF or c-Met in development. Given the small molecule and antibody antagonists to human c-Met that are in development, diagnostic antibodies are needed for the analysis of patient cancers for human c-Met.

PCT International Publication WO2009/029591 discloses a monoclonal antibody, designated MET4, that is reported to bind the ECD of human c-Met, and to be capable of staining c-Met in formalin fixed and paraffin embedded (FFPE) tumor tissues.

For evaluation of the level of expression or overexpression of human c-Met in the tumor cells of a cancer patient, either before, during, or after treatment with small molecule or antibody antagonists to human c-Met, there is a need for alternative human c-Met diagnostic antibodies that can specifically bind to an ECD of membrane localized human c-Met. Further, for evaluation of the level of expression or overexpression of human c-Met in the tumor cells of a cancer patient undergoing treatment with a therapeutic anti-c-Met agent, there is a need for human c-Met diagnostic antibodies that can specifically bind to human c-Met when the c-Met is already bound to a therapeutic anti-c-Met agent.

For a human c-Met diagnostic antibody, specificity and selectivity to human c-Met are also extremely important. Avoidance of cross-reactivity with closely related receptor tyrosine kinase family members of c-Met, such as human RON (also known as MST1R) is critical for a human c-Met diagnostic antibody. Therefore, there is also a need for human c-Met diagnostic antibodies that can specifically and selectively (e.g., without significant binding to human RON) bind to membrane localized human c-Met.

Accordingly, the present invention provides an antibody, or antigen-binding fragment thereof, that specifically binds to the ECD of human c-Met (SEQ ID NO: 24), comprising a light chain variable region (LCVR) and a heavy chain variable region (HCVR), wherein the LCVR comprises the complementarity determining regions (CDRs) LCDR1, LCDR2, and LCDR3, and the HCVR comprises the CDRs HCDR1, HCDR2, and HCDR3, wherein the LCDR1 comprises the polypeptide of RASENIYSYLA (SEQ ID NO: 1), the LCDR2 comprises the polypeptide of VYNAKPLAE (SEQ ID NO: 2), the LCDR3 comprises the polypeptide of CQHHYGTPFT (SEQ ID NO: 3), the HCDR1 comprises the polypeptide of KASGYSFTSYWMY (SEQ ID NO: 4), the HCDR2 comprises the polypeptide of GFHPGNSGTNYNQKFKG (SEQ ID NO: 5) or GFHPRNSGTNYNQKFKG (SEQ ID NO: 6), and the HCDR3 comprises the polypeptide of TRGYYYDGSFTY (SEQ ID NO: 7).

In an embodiment, the present invention provides an antibody, or antigen-binding fragment thereof, that specifically binds to the ECD of human c-Met (SEQ ID NO: 24), comprising a light chain variable region (LCVR) and a heavy chain variable region (HCVR), wherein the LCVR comprises the complementarity determining regions (CDRs) LCDR1, LCDR2, and LCDR3, and the HCVR comprises the CDRs HCDR1, HCDR2, and HCDR3, wherein the LCDR1 comprises the polypeptide of RASENIYSYLA (SEQ ID NO: 1), the LCDR2 comprises the polypeptide of VYNAKPLAE (SEQ ID NO: 2), the LCDR3 comprises the polypeptide of CQHHYGTPFT (SEQ ID NO: 3), the HCDR1 comprises the polypeptide of KASGYSFTSYWMY (SEQ ID NO: 4), the HCDR2 comprises the polypeptide of GFHPGNSGTNYNQKFKG (SEQ ID NO: 5), and the HCDR3 comprises the polypeptide of TRGYYYDGSFTY (SEQ ID NO: 7).

In an embodiment, the present invention provides an antibody, or antigen-binding fragment thereof, that specifically binds to the ECD of human c-Met (SEQ ID NO: 24), comprising a light chain variable region (LCVR) and a heavy chain variable region (HCVR), wherein the LCVR comprises the complementarity determining regions (CDRs) LCDR1, LCDR2, and LCDR3, and the HCVR comprises the CDRs HCDR1, HCDR2, and HCDR3, wherein the LCDR1 comprises the polypeptide of RASENIYSYLA (SEQ ID NO: 1), the LCDR2 comprises the polypeptide of VYNAKPLAE (SEQ ID NO: 2), the LCDR3 comprises the polypeptide of CQHHYGTPFT (SEQ ID NO: 3), the HCDR1 comprises the polypeptide of KASGYSFTSYWMY (SEQ ID NO: 4), the HCDR2 comprises the polypeptide of GFHPRNSGTNYNQKFKG (SEQ ID NO: 6), and the HCDR3 comprises the polypeptide of TRGYYYDGSFTY (SEQ ID NO: 7).

In an embodiment, the present invention provides an antibody, or antigen-binding fragment thereof, that specifically binds to the ECD of human c-Met (SEQ ID NO: 24), comprising a light chain variable region (LCVR) and a heavy chain variable region (HCVR), wherein the LCVR comprises the complementarity determining regions (CDRs) LCDR1, LCDR2, and LCDR3, and the HCVR comprises the CDRs HCDR1, HCDR2, and HCDR3, wherein the LCDR1 is the polypeptide of RASENIYSYLA (SEQ ID NO: 1), the LCDR2 is the polypeptide of VYNAKPLAE (SEQ ID NO: 2), the LCDR3 is the polypeptide of CQHHYGTPFT (SEQ ID NO: 3), the HCDR1 is the polypeptide of KASGYSFTSYWMY (SEQ ID NO: 4), the HCDR2 is the polypeptide of GFHPGNSGTNYNQKFKG (SEQ ID NO: 5) or GFHPRNSGTNYNQKFKG (SEQ ID NO: 6), and the HCDR3 is the polypeptide of TRGYYYDGSFTY (SEQ ID NO: 7).

In an embodiment, the present invention provides an antibody, or antigen-binding fragment thereof, that specifically binds to the ECD of human c-Met (SEQ ID NO: 24), comprising a light chain variable region (LCVR) and a heavy chain variable region (HCVR), wherein the LCVR comprises the complementarity determining regions (CDRs) LCDR1, LCDR2, and LCDR3, and the HCVR comprises the CDRs HCDR1, HCDR2, and HCDR3, wherein the LCDR1 is the polypeptide of RASENIYSYLA (SEQ ID NO: 1), the LCDR2 is the polypeptide of VYNAKPLAE (SEQ ID NO: 2), the LCDR3 is the polypeptide of CQHHYGTPFT (SEQ ID NO: 3), the HCDR1 is the polypeptide of KASGYSFTSYWMY (SEQ ID NO: 4), the HCDR2 is the polypeptide of GFHPGNSGTNYNQKFKG (SEQ ID NO: 5), and the HCDR3 is the polypeptide of TRGYYYDGSFTY (SEQ ID NO: 7).

In an embodiment, the present invention provides an antibody that specifically binds to the ECD of human c-Met (SEQ ID NO: 24), comprising a light chain variable region (LCVR) and a heavy chain variable region (HCVR), wherein the LCVR comprises the complementarity determining regions (CDRs) LCDR1, LCDR2, and LCDR3, and the HCVR comprises the CDRs HCDR1, HCDR2, and HCDR3, wherein the LCDR1 is the polypeptide of RASENIYSYLA (SEQ ID NO: 1), the LCDR2 is the polypeptide of VYNAKPLAE (SEQ ID NO: 2), the LCDR3 is the polypeptide of CQHHYGTPFT (SEQ ID NO: 3), the HCDR1 is the polypeptide of KASGYSFTSYWMY (SEQ ID NO: 4), the HCDR2 is the polypeptide of GFHPGNSGTNYNQKFKG (SEQ ID NO: 5), and the HCDR3 is the polypeptide of TRGYYYDGSFTY (SEQ ID NO: 7).

In an embodiment, the present invention provides an antibody, or antigen-binding fragment thereof, that specifically binds to the ECD of human c-Met (SEQ ID NO: 24), comprising a light chain variable region (LCVR) and a heavy chain variable region (HCVR), wherein the LCVR comprises the complementarity determining regions (CDRs) LCDR1, LCDR2, and LCDR3, and the HCVR comprises the CDRs HCDR1, HCDR2, and HCDR3, wherein the LCDR1 is the polypeptide of RASENIYSYLA (SEQ ID NO: 1), the LCDR2 is the polypeptide of VYNAKPLAE (SEQ ID NO: 2), the LCDR3 is the polypeptide of CQHHYGTPFT (SEQ ID NO: 3), the HCDR1 is the polypeptide of KASGYSFTSYWMY (SEQ ID NO: 4), the HCDR2 is the polypeptide of GFHPRNSGTNYNQKFKG (SEQ ID NO: 6), and the HCDR3 is the polypeptide of TRGYYYDGSFTY (SEQ ID NO: 7).

In an embodiment, the present invention provides an antibody that specifically binds to the ECD of human c-Met (SEQ ID NO: 24), comprising a light chain variable region (LCVR) and a heavy chain variable region (HCVR), wherein the LCVR comprises the complementarity determining regions (CDRs) LCDR1, LCDR2, and LCDR3, and the HCVR comprises the CDRs HCDR1, HCDR2, and HCDR3, wherein the LCDR1 is the polypeptide of RASENIYSYLA (SEQ ID NO: 1), the LCDR2 is the polypeptide of VYNAKPLAE (SEQ ID NO: 2), the LCDR3 is the polypeptide of CQHHYGTPFT (SEQ ID NO: 3), the HCDR1 is the polypeptide of KASGYSFTSYWMY (SEQ ID NO: 4), the HCDR2 is the polypeptide of GFHPRNSGTNYNQKFKG (SEQ ID NO: 6), and the HCDR3 is the polypeptide of TRGYYYDGSFTY (SEQ ID NO: 7).

In an embodiment, the present invention provides an antibody, or antigen-binding fragment thereof, that specifically binds to the ECD of human c-Met (SEQ ID NO: 24), comprising an LCVR and an HCVR, wherein the LCVR is the polypeptide of SEQ ID NO: 8, and the HCVR is the polypeptide of SEQ ID NO: 9 or SEQ ID NO: 10. In a further embodiment, the present invention provides an antibody, or antigen-binding fragment thereof, that specifically binds to the ECD of human c-Met (SEQ ID NO: 24), comprising an LCVR and an HCVR, wherein the LCVR is the polypeptide of SEQ ID NO: 8, and the HCVR is the polypeptide of SEQ ID NO: 9. In another embodiment, the present invention provides an antibody, or antigen-binding fragment thereof, that specifically binds to the ECD of human c-Met (SEQ ID NO: 24), comprising an LCVR and an HCVR, wherein the LCVR is the polypeptide of SEQ ID NO: 8, and the HCVR is the polypeptide of SEQ ID NO: 10.

In an embodiment, the present invention provides an antibody, or antigen-binding fragment thereof, that specifically binds to the ECD of human c-Met (SEQ ID NO: 24), comprising a light chain (LC) and a heavy chain (HC), wherein the LC is the polypeptide of SEQ ID NO: 11, and the HC is the polypeptide of SEQ ID NO: 12 or SEQ ID NO: 13. In a further embodiment, the present invention provides an antibody, or antigen-binding fragment thereof, that specifically binds to the ECD of human c-Met (SEQ ID NO: 24), comprising a light chain (LC) and a heavy chain (HC), wherein the LC is the polypeptide of SEQ ID NO: 11, and the HC is the polypeptide of SEQ ID NO: 12. In another embodiment, the present invention provides an antibody, or antigen-binding fragment thereof, that specifically binds to the ECD of human c-Met (SEQ ID NO: 24), comprising a light chain (LC) and a heavy chain (HC), wherein the LC is the polypeptide of SEQ ID NO: 11, and the HC is the polypeptide of SEQ ID NO: 13.

In an embodiment, the present invention provides an antibody that specifically binds to the ECD of human c-Met (SEQ ID NO: 24), comprising two light chains and two heavy chains, wherein each light chain is the polypeptide of SEQ ID NO: 11, and each heavy chain is the polypeptide of SEQ ID NO: 12. In an embodiment, the present invention provides an antibody that specifically binds to the ECD of human c-Met (SEQ ID NO: 24), comprising two light chains and two heavy chains, wherein each light chain is the polypeptide of SEQ ID NO: 11, and each heavy chain is the polypeptide of SEQ ID NO: 13.

The present invention provides compositions comprising an antibody, or antigen-binding fragment thereof, of the present invention, and an acceptable carrier, diluent, or excipient. More particularly, the compositions of the present invention further comprise one or more additional diagnostic agents.

The present invention provides a kit comprising an antibody, or antigen-binding fragment thereof, of the present invention. In an embodiment, the kit of the present invention further comprises a container comprising a secondary antibody that specifically binds to the antibody of the present invention. In a further embodiment, the kit of the present invention further comprises a container comprising a secondary antibody that specifically binds to the antibody of the present invention. Preferably, the secondary antibody is an anti-mouse IgG antibody such as an anti-mouse IgG1 antibody.

In an embodiment, the present invention provides a method of detecting human c-Met expressed or overexpressed by a human cell, comprising: (a) contacting the cell in vitro with an antibody, or antigen-binding fragment thereof, of the present invention; (b) removing any unbound or non-specifically bound antibody, or antigen-binding fragment thereof; and (c) detecting, and optionally quantifying the amount of antibody, or antigen-binding fragment thereof which is specifically bound to the ECD of human c-Met (SEQ ID NO: 24). In a further embodiment, the present invention provides a method of detecting human c-Met expressed or overexpressed by a human cell, comprising: (a) contacting the cell in vitro with an antibody, or antigen-binding fragment thereof, of the present invention; (b) removing any unbound or non-specifically bound antibody, or antigen-binding fragment thereof; and (c) detecting, and optionally quantifying the amount of antibody, or antigen-binding fragment thereof which is specifically bound to the ECD of human c-Met (SEQ ID NO: 24), wherein the human cell is formalin-fixed and paraffin-embedded. In a further embodiment, the present invention provides a method of detecting human c-Met expressed or overexpressed by a human cell, comprising: (a) contacting the cell in vitro with an antibody, or antigen-binding fragment thereof, of the present invention; (b) removing any unbound or non-specifically bound antibody, or antigen-binding fragment thereof; and (c) detecting, and optionally quantifying the amount of antibody, or antigen-binding fragment thereof, which is specifically bound to the ECD of human c-Met (SEQ ID NO: 24), and wherein the detecting is performed by direct or indirect immunohistochemistry (IHC).

In an embodiment, the present invention provides a method of determining or monitoring the response to administration of an anti-c-Met therapeutic agent in a patient, comprising: (a) measuring the amount of human c-Met with an antibody, or antigen-binding fragment thereof, of the present invention, in a first sample isolated from the patient prior to administration of the anti-c-Met therapeutic agent; (b) measuring the amount of human c-Met with an antibody, or antigen-binding fragment thereof, of the present invention in a second sample isolated from the patient after administration of the anti-c-Met therapeutic agent; (c) determining whether there has been a decrease of human c-Met in the second sample compared to the first sample, wherein a decrease in human c-Met indicates that the patient is responding to the anti-c-Met therapeutic agent.

In an embodiment, the present invention provides a method of determining or monitoring the response to administration of an anti-c-Met therapeutic agent in a patient, comprising: (a) measuring the amount of human c-Met with an antibody, or antigen-binding fragment thereof, of the present invention, in a first sample isolated from the patient prior to administration of the anti-c-Met therapeutic agent; (b) measuring the amount of human c-Met with an antibody, or antigen-binding fragment thereof, of the present invention in a second sample isolated from the patient after administration of the anti-c-Met therapeutic agent; (c) determining whether there has been a decrease of human c-Met in the second sample compared to the first sample, wherein a decrease in human c-Met indicates that the patient is responding to the anti-c-Met therapeutic agent, and wherein the anti-c-Met therapeutic agent is an antibody comprising two light chains and two heavy chains, wherein each of the light chains consists of the polypeptide of SEQ ID NO: 20 and each of the heavy chains consists of the polypeptide of SEQ ID NO: 22.

In an embodiment, the present invention provides a method of determining or monitoring the response to administration of an anti-c-Met therapeutic agent in a patient, comprising: (a) measuring the amount of human c-Met with an antibody, or antigen-binding fragment thereof, of the present invention, in a first sample isolated from the patient prior to administration of the anti-c-Met therapeutic agent; (b) measuring the amount of human c-Met with an antibody, or antigen-binding fragment thereof, of the present invention in a second sample isolated from the patient after administration of the anti-c-Met therapeutic agent; (c) determining whether there has been a decrease of human c-Met in the second sample compared to the first sample, wherein a decrease in human c-Met indicates that the patient is responding to the anti-c-Met therapeutic agent, and wherein the anti-c-Met therapeutic agent is N-(3-Fluoro-4-(1-methyl-6-(1H-pyrazol-4-yl)-1H-indazol-5-yloxy)phenyl)-1-(4-fluorophenyl)-6-methyl-2-oxo-1,2-dihydropyridine-3-carboxamide or 6-(1-Methyl-1H-pyrazol-4-yl)-3-(2-methyl-2H-indazol-5-ylthio)-[1,2,4]triazolo[4,3-b]pyridazine.

In an embodiment, the present invention provides an antibody of the present invention, for use in diagnosis, prognosis and/or prediction of a cancer treatment response with an anti-c-Met therapeutic antibody or small molecule c-Met therapeutic compound.

In an embodiment, the present invention provides use of an antibody, or antigen-binding fragment thereof, of the present invention, for:

(a) detecting, and optionally quantifying human c-Met in or on a human cell;

(b) detecting, and optionally quantifying human c-Met expressing or overexpressing tumor cells in a patient;

(c) detecting and, optionally, quantifying human c-Met expressing or overexpressing circulating tumor cells in a blood sample of a patient;

(d) detecting and, optionally, quantifying human c-Met expressing or overexpressing tumor cells in a bodily fluid from a cancer patient;

(e) assessing whether an individual has cancer of a tissue or organ wherein human c-Met is expressed or overexpressed;

(f) selecting a patient having a tumor suitable for treatment with an anti-c-Met therapeutic agent; or (g) determining response to treatment with an anti-c-Met therapeutic agent.

In a further embodiment, the present invention provides use of an antibody, or antigen-binding fragment thereof, of the present invention, wherein the detection, and, optionally, the quantification of human c-Met is performed by IHC. In a further embodiment, the present invention provides use of an antibody, or antigen-binding fragment thereof, of the present invention, wherein the anti-c-Met agent is an antibody comprising two light chains and two heavy chains, wherein each of the light chains consists of the polypeptide of SEQ ID NO: 20 and each of the heavy chains consists of the polypeptide of SEQ ID NO: 22, or wherein the anti-c-Met agent is N-(3-Fluoro-4-(1-methyl-6-(1H-pyrazol-4-yl)-1H-indazol-5-yloxy)phenyl)-1-(4-fluorophenyl)-6-methyl-2-oxo-1,2-dihydropyridine-3-carboxamide or 6-(1-Methyl-1H-pyrazol-4-yl)-3-(2-methyl-2H-indazol-5-ylthio)-[1,2,4]triazolo[4,3-b]pyridazine.

In an embodiment, the present invention provides a method of selecting a patient, having a tumor in which human c-Met is expressed or overexpressed, for treatment with an anti-c-Met therapeutic antibody or small molecule c-Met therapeutic compound, comprising: (a) contacting a sample of the tumor with an antibody, or antigen-binding fragment thereof, of the present invention; (b) removing any unbound or non-specifically bound antibody, or antigen-binding fragment thereof; and (c) detecting and, optionally, quantifying the amount of antibody, or antigen-binding fragment thereof, which is specifically bound to the ECD of human c-Met, wherein the presence of the antibody, or antigen-binding fragment thereof, specifically bound to the ECD of human c-Met identifies the patient as being appropriate for treatment with the anti-c-Met therapeutic antibody or small molecule c-Met therapeutic compound.

In an embodiment, the present invention provides a method of predicting a patient's response to administration of an anti-c-Met therapeutic antibody or small molecule c-Met therapeutic compound, comprising: (a) contacting a sample of a tumor from the patient with an antibody, or antigen-binding fragment thereof, of the present invention; (b) removing any unbound or non-specifically bound antibody, or antigen-binding fragment thereof; and (c) detecting and, optionally, quantifying the amount of antibody, or antigen-binding fragment thereof, which is specifically bound to the ECD of human c-Met, wherein the presence of the antibody, or antigen-binding fragment thereof, specifically bound to the ECD of human c-Met indicates that the patient will likely respond to the administration of an anti-c-Met therapeutic antibody or small molecule c-Met therapeutic compound.

In an embodiment, the present invention provides a method of treating cancer, comprising: (a) selecting a patient in need of treatment thereof, wherein the patient has a tumor in which human c-Met is expressed or overexpressed as determined by detecting human c-Met with an antibody, or antigen-binding fragment thereof, of the present invention; and (b) treating the patient with an anti-c-Met therapeutic agent, wherein the anti-c-Met therapeutic agent is an antibody comprising two light chains and two heavy chains, wherein each of the light chains consists of the polypeptide of SEQ ID NO: 20 and each of the heavy chains consists of the polypeptide of SEQ ID NO: 22, or wherein the anti-c-Met agent is N-(3-Fluoro-4-(1-methyl-6-(1H-pyrazol-4-yl)-1H-indazol-5-yloxy)phenyl)-1-(4-fluorophenyl)-6-methyl-2-oxo-1,2-dihydropyridine-3-carboxamide or 6-(1-Methyl-1H-pyrazol-4-yl)-3-(2-methyl-2H-indazol-5-ylthio)-[1,2,4]triazolo[4,3-b]pyridazine. In various embodiments of the methods of the present invention, the cancer being treated is gastric cancer, non-small cell lung cancer, colon, cholangiocarcinoma, head and neck cancer, or kidney cancer. In various embodiments of the methods of the present invention, the detecting human c-Met is with an antibody comprising two light chains and two heavy chains, wherein each light chain is the polypeptide of SEQ ID NO: 11, and each heavy chain is the polypeptide of SEQ ID NO: 12, or with an antibody comprising two light chains and two heavy chains, wherein each light chain is the polypeptide of SEQ ID NO: 11, and each heavy chain is the polypeptide of SEQ ID NO: 13.

In an embodiment, the present invention provides a method of treating cancer in a patient, comprising testing for the presence of human c-Met in a biological sample from the patient and administering a therapeutically effective amount of an anti-c-Met therapeutic agent to the patient if the sample tests positive for human c-Met as determined by detection with an antibody, or antigen-binding fragment thereof, of the present invention, and wherein the anti-c-Met therapeutic agent is an antibody comprising two light chains and two heavy chains, wherein each of the light chains consists of the polypeptide of SEQ ID NO: 20 and each of the heavy chains consists of the polypeptide of SEQ ID NO: 22, or wherein the anti-c-Met agent is N-(3-Fluoro-4-(1-methyl-6-(1H-pyrazol-4-yl)-1H-indazol-5-yloxy)phenyl)-1-(4-fluorophenyl)-6-methyl-2-oxo-1,2-dihydropyridine-3-carboxamide or 6-(1-Methyl-1H-pyrazol-4-yl)-3-(2-methyl-2H-indazol-5-ylthio)-[1,2,4]triazolo[4,3-b]pyridazine. In various embodiments of the methods of the present invention, the cancer being treated is gastric cancer, non-small cell lung cancer, colon, cholangiocarcinoma, head and neck cancer, or kidney cancer. In various embodiments of the methods of the present invention, the detecting human c-Met is with an antibody comprising two light chains and two heavy chains, wherein each light chain is the polypeptide of SEQ ID NO: 11, and each heavy chain is the polypeptide of SEQ ID NO: 12, or with an antibody comprising two light chains and two heavy chains, wherein each light chain is the polypeptide of SEQ ID NO: 11, and each heavy chain is the polypeptide of SEQ ID NO: 13. In various embodiments of the methods of the present invention, the biological sample is formalin-fixed and paraffin-embedded.

In an embodiment, the present invention provides a method of treating cancer in a patient, comprising administering a therapeutically effective amount of an anti-c-Met therapeutic agent to the patient provided that the patient is selected for treatment if a biological sample from the patient tests positive for human c-Met as determined by detection with an antibody, or antigen-binding fragment thereof, of the present invention, and wherein the anti-c-Met therapeutic agent is an antibody comprising two light chains and two heavy chains, wherein each of the light chains consists of the polypeptide of SEQ ID NO: 20 and each of the heavy chains consists of the polypeptide of SEQ ID NO: 22, or wherein the anti-c-Met agent is N-(3-Fluoro-4-(1-methyl-6-(1H-pyrazol-4-yl)-1H-indazol-5-yloxy)phenyl)-1-(4-fluorophenyl)-6-methyl-2-oxo-1,2-dihydropyridine-3-carboxamide or 6-(1-Methyl-1H-pyrazol-4-yl)-3-(2-methyl-2H-indazol-5-ylthio)-[1,2,4]triazolo[4,3-b]pyridazine. In various embodiments of the methods of the present invention, the cancer being treated is gastric cancer, non-small cell lung cancer, colon, cholangiocarcinoma, head and neck cancer, or kidney cancer. In various embodiments of the methods of the present invention, the detecting human c-Met is with an antibody comprising two light chains and two heavy chains, wherein each light chain is the polypeptide of SEQ ID NO: 11, and each heavy chain is the polypeptide of SEQ ID NO: 12, or with an antibody comprising two light chains and two heavy chains, wherein each light chain is the polypeptide of SEQ ID NO: 11, and each heavy chain is the polypeptide of SEQ ID NO: 13. In various embodiments of the methods of the present invention, the biological sample is formalin-fixed and paraffin-embedded.

In an embodiment, the present invention provides an anti-c-Met therapeutic agent, for use in the treatment of cancer comprising (a) selecting a patient in need of treatment thereof, wherein the patient has a tumor in which human c-Met is expressed or overexpressed as determined by detecting human c-Met with an antibody, or antigen-binding fragment thereof, of the present invention, and (b) treating the patient with the anti-c-Met therapeutic agent, wherein the anti-c-met therapeutic agent is an antibody comprising two light chains and two heavy chains, wherein each of the light chains consists of the polypeptide of SEQ ID NO: 20 and each of the heavy chains consists of the polypeptide of SEQ ID NO: 22, or wherein the anti-c-Met therapeutic agent is N-(3-Fluoro-4-(1-methyl-6-(1H-pyrazol-4-yl)-1H-indazol-5-yloxy)phenyl)-1-(4-fluorophenyl)-6-methyl-2-oxo-1,2-dihydropyridine-3-carboxamide or 6-(1-Methyl-1H-pyrazol-4-yl)-3-(2-methyl-2H-indazol-5-ylthio)-[1,2,4]triazolo[4,3-b]pyridazine. In various embodiments of the present invention for use in the treatment of cancer, the cancer is gastric cancer, non-small cell lung cancer, colon, cholangiocarcinoma, head and neck cancer, or kidney cancer. In various embodiments of the present invention for use in the treatment of cancer, human c-Met is detected with an antibody comprising two light chains and two heavy chains, wherein each light chain is the polypeptide of SEQ ID NO: 11, and each heavy chain is the polypeptide of SEQ ID NO: 12, or with an antibody comprising two light chains and two heavy chains, wherein each light chain is the polypeptide of SEQ ID NO: 11, and each heavy chain is the polypeptide of SEQ ID NO: 13.

In an embodiment, the present invention provides an anti-c-Met therapeutic agent, for use in treating cancer, comprising performing an in vitro assay using a biological sample from a patient, determining the presence of human c-Met by detection with an antibody, or antigen-binding fragment thereof, of the present invention, and administering a therapeutically effective amount of the anti-c-Met therapeutic agent to the patient if human c-Met is present, wherein the anti-c-Met therapeutic agent is an antibody comprising two light chains and two heavy chains, wherein each of the light chains consists of the polypeptide of SEQ ID NO: 20 and each of the heavy chains consists of the polypeptide of SEQ ID NO: 22, or wherein the anti-c-Met therapeutic agent is N-(3-Fluoro-4-(1-methyl-6-(1H-pyrazol-4-yl)-1H-indazol-5-yloxy)phenyl)-1-(4-fluorophenyl)-6-methyl-2-oxo-1,2-dihydropyridine-3-carboxamide or 6-(1-Methyl-1H-pyrazol-4-yl)-3-(2-methyl-2H-indazol-5-ylthio)-[1,2,4]triazolo[4,3-b]pyridazine. In various embodiments of the present invention for use in the treatment of cancer, the cancer is gastric cancer, non-small cell lung cancer, colon, cholangiocarcinoma, head and neck cancer, or kidney cancer. In various embodiments of the present invention for use in the treatment of cancer, human c-Met is detected with an antibody comprising two light chains and two heavy chains, wherein each light chain is the polypeptide of SEQ ID NO: 11, and each heavy chain is the polypeptide of SEQ ID NO: 12, or with an antibody comprising two light chains and two heavy chains, wherein each light chain is the polypeptide of SEQ ID NO: 11, and each heavy chain is the polypeptide of SEQ ID NO: 13.

In various embodiments of the methods of the present invention, the detection of binding of an antibody, or antigen-binding fragment thereof, of the present invention to the ECD of human c-Met is performed by immunoassay techniques, such as IHC, flow cytometry, western blotting, or ELISA. More preferably, the detection of binding of an antibody, or antigen-binding fragment thereof, of the present invention to the ECD of human c-Met is performed by IHC.

In further embodiments of this aspect of the invention, the human cell can be formalin fixed and paraffin-embedded, and the detecting can be performed by direct or indirect IHC. Indirect IHC can comprise the use of a secondary, enzyme-conjugated monoclonal antibody or antigen-binding fragment thereof that binds the c-Met or competing monoclonal antibody or antigen-binding fragment thereof, and c-Met can be detected by the use of a chromogenic substrate of the enzyme.

In another embodiment, the antibodies, or antigen-binding fragments thereof, of the present invention may be used to detect circulating tumor cells (CTCs). CTCs are tumor cells that are shed from tumors, survive within the bloodstream during transit and initiate a new growth in distant sites. Detecting CTCs is useful as CTCs can be found in patients before a tumor is detected. CTCs are also found in a significant proportion of patients when a carcinoma recurs, and CTCs persist in some patients after removal of the primary tumor. Evidence suggests that CTCs are derived from clones in the primary tumor as well as metastatic tumors and that they may reflect the tumor burden at all stages of tumor progression. Thus, in addition to a potential role in early diagnosis and prognostication, CTCs may play a major role in characterizing genetic and phenotypic changes with tumor progression, thereby helping to guide targeted therapy. More particularly, the antibodies, or antigen-binding fragments thereof, of the present invention may be useful in assays that can capture, identify, and/or quantify CTCs such as, e.g., the CellSearch® CTC Test (Veridex LLC, San Diego, Calif.), Magnetic Activated Cell Sorting System (MACS®, Miltenyi Biotec GmbH, Germany), Dynal Magnetic Beads® (Invitrogen), EasySep® (Stem Cell Technologies, Vancouver Canada), CTC Chips (On-Q-ity, Waltham, Mass.), or any other test known in the art for the isolation and detection of CTCs such as those described in Sleijfer, et al. *Circulating tumour cell detection on its way to routine diagnostic implementation?* Eur J Cancer, 43 (18):2645-50 (2007); Lacroix M., *Significance, detection and markers of disseminated breast cancer cells.* Endocr Relat Cancer., 13 (4):1033-67 (2006); and Pantel, et al., *Detection, clinical relevance and specific biological properties of disseminating tumour cells.* Nat Rev Cancer, 8 (5):329-40 (2008)). Presently, CellSearch® CTC is the only diagnostic test approved by the USFDA as an automated test to detect and enumerate circulating tumor cells (Fed. Reg. 69(91):26036-38 (2004). Results from CellSearch® tests have been used to monitor disease progression and therapeutic efficacy in metastatic prostate (Danila, et al., *Circulating tumor cell number and prognosis in progressive castration-resistant prostate cancer.* Clin Cancer Res., 13(23):7053-58 (2007)), colorectal (Cohen, et al., *Isolation and characterization of circulating tumor cells in patients with metastatic colorectal cancer.* Clin Colorectal Cancer 6 (2):125-32 (2006)), and breast (Cristofanilli, et al. *Circulating tumor cells, disease progression, and survival in metastatic breast cancer.* N Engl J Med., 351(8):781-91 (2004)) cancer. An antibody, or antigen-binding fragment thereof, of the present invention, e.g., Antibody I or II, described herein and in particular in Table 1 below, can be used in such methods, e.g., CellSearch® tests, and in some cases performed at the start of therapy and any time during the course of treatment for a c-Met-mediated-cancer. Preferably, an antibody, or antigen-binding fragment thereof, of the present invention may be used in such methods along with antibodies specific for other polypeptides including, but not limited to, EPCAM, DAPI, CD45, and/or cytokeratin (including, but not limited to, cytokeratin 7, 8, 18, and/or 19). Information generated from such testing may be useful for its prognostic value by allowing, e.g., monitoring of disease progression and therapeutic efficacy and may allow earlier (and ongoing) treatment decisions. Further, by permitting simultaneous binding of a detectably labeled antibody, or antigen-binding fragment thereof, of the present invention and a therapeutic anti-c-Met antibody (such as disclosed in WO/2010/059654) a break in treatment with a therapeutic anti-c-Met antibody, i.e., "washing out" the therapeutic antibody to allow the diagnostic antibody to bind c-Met, is not required. Consequently, an antibody, or antigen-binding fragment thereof, of the invention permits uninterrupted therapeutic treatment concomitantly with diagnostic monitoring, as necessary.

As used herein, "c-Met" or "human c-Met" refers to human c-Met; the structure of c-Met is depicted schematically as:

Extracellular Domain (ECD)        Intracellular Domain

SEMA - PSI - 4 IPT - TM - JM - KD - intracellular tail

SEMA: Sema domain
PSI: Plexin, Semaphorins, and Integrins domain
IPT: 4 Immunoglobulins, Plexins, and Transcription (IPT) factor domains
TM: Transmembrane region
JM: Juxtamembrane domain
KD: Kinase domain For the human c-Met ECD, the mature protein is the polypeptide of SEQ ID NO: 24. The SEMA domain consists of approximately 500 amino acid residues at the N-terminus of human c-Met, and contains the α-chain (amino acid residues 1-283 of SEQ ID NO: 24, i.e., (SEQ ID NO: 25) and part of the β-chain (amino acid residues 284-495 of SEQ ID NO: 24, i.e., (SEQ ID NO: 26)).

In an embodiment, an antibody, or antigen-binding fragment thereof, of the present invention specifically binds to the ECD of human c-Met. In another embodiment, an antibody, or antigen-binding fragment thereof, of the present invention specifically binds to the IPT domain. In a further embodiment, an antibody, or antigen-binding fragment thereof, of the present invention specifically binds within amino acids 517-538, inclusive, of the mature human c-Met ECD (SEQ ID NO: 24).

The general structure of an "antibody" is very well-known in the art. For an antibody of the IgG type, there are four amino acid chains (two "heavy" chains and two "light" chains) that are cross-linked via intra- and inter-chain disulfide bonds. When expressed in certain biological systems, antibodies having unmodified human Fc sequences are glycosylated in the Fc region. Antibodies may be glycosylated at other positions as well. One of skill in the art will appreciate that antibodies of the present invention may contain such glycosylation. The subunit structures and three-dimensional configurations of antibodies are well known in the art. Each heavy chain is comprised of an N-terminal heavy chain variable region ("HCVR") and a heavy chain constant region ("HCCR"). The heavy chain constant region is comprised of three domains (CH1, CH2, and CH3) for IgG, IgD, and IgA; and 4 domains (CH1, CH2, CH3, and CH4) for IgM and IgE. Each light chain is comprised of a light chain variable region ("LCVR") and a light chain constant region ("LCCR"). The variable regions of each light/heavy chain pair form the antibody binding site.

An antibody, or antigen-binding fragment thereof, of the present invention can be produced using techniques well known in the art, e.g., recombinant technologies, phage display technologies, synthetic technologies, or combinations of such technologies or other technologies readily known in the art. Methods for producing and purifying antibodies and antigen-binding fragments are well known in the art and can be found, for example, in Harlow and Lane (1988) *Antibodies, A Laboratory Manual*, Cold Spring Harbor Laboratory Press, Cold Spring Harbor, N.Y., chapters 5-8 and 15, ISBN 0-87969-314-2.

An antibody, or antigen-binding fragment thereof, of the present invention is an engineered antibody that has been designed to have frameworks, hinge regions, and constant regions of human origin that are identical with or substantially identical (substantially human) with frameworks and constant regions derived from human genomic sequences. Fully human frameworks, hinge regions, and constant regions are those human germline sequences as well as sequences with naturally-occurring somatic mutations and/or those with engineered mutations. An antibody, or antigen-binding fragment thereof, of the present invention may comprise framework, hinge, or constant regions derived from a fully human framework, hinge, or constant region containing one or more amino acid substitutions, deletions, or additions therein. Further, an antibody, or antigen-binding fragment thereof, of the present invention is substantially non-immunogenic in humans.

The antibodies, or antigen-binding fragments thereof, of the present invention may be useful as diagnostics to aid in identification of cancer patients with tumor cells expressing relatively high levels of c-Met. Furthermore, such antibodies, or antigen-binding fragments thereof, may be used to monitor and, optionally, optimize a cancer patient's treatment with c-Met targeted therapeutic agents, such as the small molecule c-Met therapeutic compounds described in WO2010/011538 and U.S. patent application Ser. No. 13/188,496, for example, Structures 1 and 2 hereafter, as well as anti-c-Met therapeutic antibodies, such as those described in WO2010/059654 and WO2006/015371, including, but not limited to, C8-H241 and MetMAb. More specifically, the antibodies, or antigen-binding fragments thereof, of the present invention may be used to monitor, and optionally optimize, a cancer patient's treatment with the anti-c-Met therapeutic antibody C8-H241 (Chemical Abstracts Service (CAS) #1365287-97-3). The anti-c-Met antibody C8-H241 comprises two light chains and two heavy chains, wherein each of the light chains consists of the polypeptide of SEQ ID NO: 20 and each of the heavy chains consists of the polypeptide of SEQ ID NO: 22. Alternatively, the anti-c-Met therapeutic antibody comprises two light chains and two heavy chains, wherein each of the light chains consists of the polypeptide of SEQ ID NO: 20 and each of the heavy chains consists of the polypeptide of SEQ ID NO: 21. More specifically, the antibodies, or antigen-binding fragments thereof, of the present invention may be used to monitor, and optionally optimize, a cancer patient's treatment with the anti-c-Met therapeutic antibody MetMAb. As used herein, "MetMAb" is intended to mean a humanized one-armed 5D5 (OA-5D5; onartuzumab, CAS #1133766-06-9) antibody having the light chain as shown in SEQ ID NO: 27 and the heavy chain as shown in SEQ ID NO: 28. MetMAb may be produced in mammalian cells or *E. coli*; mammalian cells may include HEK 293 EBNA cells. More specifically, the antibodies, or antigen-binding fragments thereof, of the present invention may be used to monitor, and, optionally, optimize, a cancer patient's treatment with the small molecule c-Met therapeutic compounds shown below as Structure 1 and Structure 2, or pharmaceutically acceptable salts thereof.

Structure 1: N-(3-Fluoro-4-(1-methyl-6-(1H-pyrazol-4-yl)-1H-indazol-5-yloxy)phenyl)-1-(4-fluorophenyl)-6-methyl-2-oxo-1,2-dihydropyridine-3-carboxamide

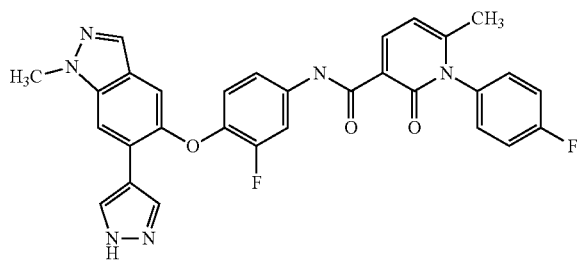 [SMILES: Cc1ccc(C(=O)Nc2ccc(Oc3cc4cnn(C)c4cc3-c3cn[nH]c3)c(F)c2)c(=O)n1-c1ccc(F)cc1]

Structure 2: 6-(1-Methyl-1H-pyrazol-4-yl)-3-(2-methyl-2H-indazol-5-ylthio)-[1,2,4]triazolo[4,3-b]pyridazine

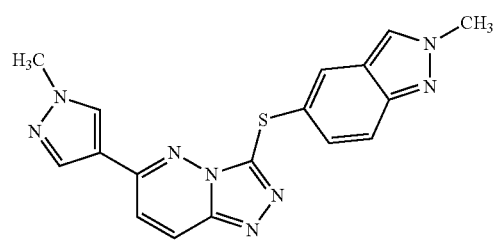 [SMILES: Cn1cc(-c2ccc3nnc(Sc4ccc5nn(C)cc5c4)n3n2)cn1]

The phrase "specifically binds" as used herein in reference to the affinity of a c-Met antibody, or antigen-binding fragment thereof, for the ECD of human c-Met is intended to mean, unless indicated otherwise, a $K_D$ of less than about $1 \times 10^{-8}$ M, preferably, less than about $1 \times 10^{-9}$ M as determined by common methods known in the art, including by use of a surface plasmon resonance (SPR) biosensor at 25° C. essentially as described herein. The term "selective" used herein in reference to an antibody, or antigen-binding fragment thereof, of the present invention refers to an antibody, or antigen-binding fragment thereof, that binds the ECD of human c-Met with a $K_D$ about 1000-, 500-, 200-, 100-, 50-, 10-, or about 5-fold lower than the antibody, or antigen-binding fragment thereof, binds at least one member of the human tyrosine kinase family, including, but not limited to, human RON, as measured by surface plasmon resonance at 25° C. Additionally, or alternatively, a c-Met selective antibody, or antigen-binding fragment thereof, of the present invention binds to the ECD of human c-Met but does not bind or only minimally binds to at least one member of the human tyrosine kinase family, including, but not limited to human RON, when assayed by the immunoassay methods described in Examples 3-7 herein below.

Human c-Met is overexpressed in or on a human cell, CTC, or tumor tissue sample when the quantity of human c-Met is determined to be significantly greater for the human cell, CTC, or tumor tissue sample than the quantity of human c-Met in normal human cells or non-tumor human tissue.

The antibodies, or antigen-binding fragments thereof, disclosed herein are useful for detecting expression, overexpression, or the level of human c-Met present in or on cells, or in or on cells in tissues, organs, bodily fluids, etc., and in diagnostic, prognostic, and/or patient monitoring procedures. The term "bodily fluid" refers to any fluid or other material derived from the body of a normal or diseased subject, such as blood, serum, plasma, lymph, bone marrow, urine, saliva, tears, cerebrospinal fluid, milk, amniotic fluid, bile, urine, bronchial fluid, ascites fluid, pus, and any other biological product. Also included within the meaning of this term is an organ or tissue extract, and a culture fluid in which any cells or tissue preparation from a subject have been incubated.

There are well-known methods in the art that a skilled artisan may use to form stable, detectable antigen-antibody complexes (see, e.g., *Antibodies, A Laboratory Manual* by Harlow and Lane (current edition), Cold Spring Harbor Laboratory Press, Cold Spring Harbor, N.Y., for conditions permitting formation of detectable antigen/antibody complexes). In particular, WO 2010/059654 describes exemplary conditions which may permit binding of the antibodies, or antigen-binding fragments thereof, of the present invention including, but not limited to, the antibodies referred to herein as Antibody I and Antibody II. A composition comprising an antibody, or antigen-binding fragment thereof, of the present invention bound to the ECD of human c-Met may also be detected, labeled, and/or identified using methods taught herein or generally known in the art, including, but not limited to, such methods disclosed in Harlow and Lane, ibid, or WO 2010/059654.

A particular protein such as human c-Met can be measured by a variety of immunoassay methods including, e.g., without limitation, competitive and noncompetitive assay systems using techniques such as, e.g., without limitation, western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, and protein A immunoassays. For a review of immunological and immunoassay procedures in general, see Stites and Terr (eds.) (1991) *Basic and Clinical Immunology* (7th ed.). Moreover, the immunoassays of the invention can be performed in many configurations, which are reviewed extensively in Maggio (ed.) (1980) *Enzyme Immunoassay* CRC Press, Boca Raton, Fla.; Gosling J P 2000 *Immunoassays: A Practical Approach* (Practical Approach Series) Oxford Univ Press; Diamandis & Christopoulus, 1996 *Immunoassay* Academic Press, San Diego, Calif.; Tijan (1985) "Practice and Theory of Enzyme Immunoassays," *Laboratory Techniques in Biochemistry and Molecular Biology*, Elsevier Science Publishers B.V., Amsterdam; Wild, D. (Ed.), 2001 *The Immunoassay Handbook* (2nd edition) Nature Pub Group; James T. Wu, 2000 *Quantitative Immunoassay: A Practical Guide for Assay Establishment, Troubleshooting, and Clinical Application*, Amer Assn for Clinical Chemistry, Brousseau & Beaudet (Eds.) *Manual of Immunological Methods* CRC Press Boca Raton, Fla.; and Harlow and Lane *Antibodies, A Laboratory Manual*, supra. See also Chan (ed.) (1987) *Immunoassay: A Practical Guide* Academic Press, Orlando, Fla.; Price and Newman (eds.) (1991) *Principles and Practice of Immunoassays* Stockton Press, NY; and Ngo (ed.) (1988) *Non-isotopic Immunoassays* Plenum Press, NY.

Immunoassays can be performed by a variety of art-known methods. In brief, immunoassays to measure the human c-Met ECD can be either competitive or noncompetitive binding assays. In competitive binding assays, the sample to be analyzed competes with a labeled analyte for specific binding sites on a capture agent bound to a solid surface. Preferably, the capture agent is an antibody specifically reactive with the human c-Met ECD as described herein. The concentration of labeled analyte bound to the capture agent is inversely proportional to the amount of free analyte present in the sample.

In a competitive binding immunoassay, the target protein present in the sample (i.e., the human c-Met ECD) competes with labeled protein for binding to an antibody of the present invention. The antibody of the present invention may be bound to a solid surface to effect separation of bound-labeled protein from the unbound-labeled protein. Alternately, the competitive binding assay may be conducted in liquid phase and a variety of techniques known in the art may be used to separate the bound-labeled protein from the unbound-labeled protein. Following separation, the amount of bound labeled protein is determined. The amount of protein present in the sample is inversely proportional to the amount of labeled protein binding.

Alternatively, a homogeneous immunoassay may be performed in which a separation step is not needed. In these immunoassays, the label on the protein is altered by the binding of the protein to its specific binding composition. This alteration in the labeled protein results in a decrease or increase in the signal emitted by label, so that measurement of the label at the end of the immunoassay allows for detection or quantitation of the protein.

Competitive assays are also particularly useful, where the cells are contacted and incubated with a labeled antibody having known binding affinity to the protein, such as a $^{125}$I-labeled antibody, and a test sample whose binding affinity to the binding composition is being measured. The bound and free-labeled binding compositions are then separated to assess the degree of protein binding. The amount of test compound bound is inversely proportional to the amount of labeled binding partner binding to the known source. Any one of numerous techniques can be used to separate bound from free protein to assess the degree of protein binding. This separation step could typically involve a procedure such as adhesion to filters followed by washing, adhesion to plastic followed by washing, or centrifugation of the cell membranes. Viable cells could also be used to screen for the effects of drugs on a human c-Met mediated function (e.g., second messenger levels, such as, e.g., cell proliferation; inositol phosphate pool changes, transcription using a luciferase-type assay; and others). Some detection methods allow for elimination of a separation step, e.g., a proximity-sensitive detection system.

Qualitative or quantitative analysis of human c-Met may also be determined by a variety of noncompetitive immunoassay methods using the antibodies, or antigen-binding fragments thereof, of the present invention. For example, a two-site, solid phase sandwich immunoassay may be used. In this type of assay, an antibody is attached to a solid support. A second protein-binding composition, which may also be an antibody, and which specifically bind the protein at a different site, is labeled. After binding at both sites on the protein has occurred, the unbound-labeled binding composition is removed and the amount of labeled binding composition bound to the solid phase is measured. The amount of labeled binding composition bound is directly proportional to the amount of protein in the sample.

EXAMPLE 1

Antibody Expression and Purification

The polypeptides of the variable regions of the heavy chain and light chain, the complete heavy chain and light chain amino acid sequences of Antibody I and II, and the nucleotide sequences encoding the same, are listed below in the section entitled "Amino Acid and Nucleotide Sequences." In addition, the light chain and heavy chain CDR polypeptides are shown in Table 1.

The antibodies, or antigen-binding fragments thereof, of the present invention, including, but not limited to, Antibodies I and II, may be transiently expressed in HEK293 EBNA cells (Edge BioSystems, #90500130) using standard transfection procedures. Transfected cells are cultured in standard serum-free medium containing geneticin (G418) and tobramycin for 48 to 120 hours at 37° C. after transfection. The antibody may be purified on a 60 ml rProtein A Sepharose column (Amersham Biosciences; #17-1279-04) by following well-known procedures and/or the manufacturer's instructions, and further concentrated and purified by size exclusion chromatography (XK50/60 Superdex200, Pharmacia) with phosphate buffered saline (PBS), pH 7.4, as the mobile phase. Next, the antibody preparation may be filtered using a Millex-GV, PVDF membrane, 0.22 μmm, (Millipore; #SLGV033RS) and stored at 4 to 8° C.

TABLE 1

| | | SEQ ID NOs | | |
|---|---|---|---|---|
| Antibody | Light Chain | Heavy Chain | LCVR | HCVR |
| I | 11 | 12 | 8 | 9 |
| II | 11 | 13 | 8 | 10 |

TABLE 1-continued

| | SEQ ID NOs | | |
|---|---|---|---|
| Antibody | LCDR1 | LCDR2 | LCDR3 |
| I | RASENIYSYLA (SEQ ID NO: 1) | VYNAKPLAE (SEQ ID NO: 2) | CQHHYGTPFT (SEQ ID NO: 3) |
| II | RASENIYSYLA (SEQ ID NO: 1) | VYNAKPLAE (SEQ ID NO: 2) | CQHHYGTPFT (SEQ ID NO: 3) |

| Antibody | HCDR1 | HCDR2 | HCDR3 |
|---|---|---|---|
| I | KASGYSFTSYWMY (SEQ ID NO: 4) | GFHPGNSGTNYNQ KFKG (SEQ ID NO: 5) | TRGYYYDGSFTY (SEQ ID NO: 7) |
| II | KASGYSFTSYWMY (SEQ ID NO: 4) | GFHPRNSGTNYNQ KFKG (SEQ ID NO: 6) | TRGYYYDGSFTY (SEQ ID NO: 7) |

EXAMPLE 2

Binding Kinetics and Affinity of Antibodies I and II

The binding kinetics and affinity of an antibody, or antigen-binding fragment thereof, of the present invention to human c-Met ECD may be determined by use of a surface plasmon resonance biosensor such as a BIAcore® 2000, BIAcore® 3000, or a BIAcore® T100 (GE Health Care, Piscataway, N.J.) according to methods known in the art. Except as noted, all reagents and materials may be purchased from GE Healthcare, and measurements may be performed at 25° C. The BIAcore® instrument may be primed with HBS-EP+ running buffer (10 mM N-2-hydroxyethylpiperazine-N'-2-ethanesulfonic acid (HEPES) pH 7.4, 150 mM NaCl, 3 mM EDTA, 0.05% surfactant P20; #BR-1006-69) and analysis temperature set at 25° C. A CMS chip containing immobilized goat anti-mouse Fc antibody (generated using standard NHS-EDC amine coupling) on all four flow cells may be used to employ a capture methodology. The antibodies, or antigen-binding fragments thereof, of the present invention may be prepared at 5 microgram/mL by dilution into HBS-EP+ running buffer. The c-Met-ECD with Fc and Flis tag (c-Met-ECD-Fc-Flis) can be expressed from CHO cells and purified for this analysis (SEQ ID NO: 23). Human c-Met-ECD-Fc-Flis may be prepared at a final concentrations ranging from 200 nM to 1.56 nM (with 2 fold dilutions) by dilution into HBS-EP+ running buffer. Each analysis cycle may consist of (1) capturing samples of the antibodies, or antigen-binding fragments thereof, of the present invention on flow cells 2, 3, and 4, (2) injection of 250 microliter (300 sec) of human c-Met-ECD over all flow cells at 50 microliter/min, (3) return to HBS-EP+ running buffer flow for 20 min to monitor dissociation phase, (4) regeneration of chip surfaces with a 30 microliter (36 sec) injection of glycine, pH 1.5, (5) equilibration of chip surfaces with a 50 microliter (60 sec) injection of HBS-EP+ running buffer. Data may be processed using standard double-referencing and fit to a 1:1 binding model using BIAcore® 2000 Evaluation software, version 4.1, to determine the association rate ($k_{on}$, $M^{-1}s^{-1}$ units), dissociation rate ($k_{off}$, $s^{-1}$ units), and $R_{max}$ (RU units). The equilibrium dissociation constant ($K_D$) may be calculated from the relationship $K_D = k_{off}/k_{on}$, and is in molar units.

In experiments performed essentially as described in this Example 2, Antibodies I and II bind human c-Met-ECD with very high binding affinity ($K_D$) (see Table 2). Antibody II binds c-Met-ECD with greater than 5× binding affinity compared to Antibody I.

TABLE 2

Antibodies I and II Binding Kinetics and Affinity to human c-Met-ECD-Fc-Flis

| Antibody | $k_{on}$ Avg +/− SD $M^{-1} s^{-1} (10^5)$ | $k_{off}$ Avg +/− SD $s^{-1} (10^{-4})$ | $K_D$ Avg +/− SD nM | n |
|---|---|---|---|---|
| I | 1.23 ± 0.06 | 3.02 ± 0.01 | 2.47 ± 0.14 | 2 |
| II | 1.25 ± 0.06 | 0.46 ± 0.02 | 0.37 ± 0.04 | 2 |

EXAMPLE 3

Antibodies I and II Simultaneously Bind ECD of Human c-Met with C8-H241

Surface Plasmon Resonance

To determine if an antibody, or antigen-binding fragment thereof, of the present invention can bind the ECD of human c-Met at the same time as an anti-c-Met therapeutic antibody (such as, e.g., C8-H241, disclosed in WO/2010/059654), a binding experiment may be performed using a surface plasmon resonance biosensor such as a BIAcore® 2000, BIAcore® 3000, or a BIAcore® T100 (GE Health Care, Piscataway, N.J.) according to methods known in the art. Except as noted, all reagents and materials may be purchased from BIAcore®. The c-Met-ECD with Fc and Flis tag (c-Met-ECD-Fc-Flis) can be expressed from CHO cells and purified for this analysis (SEQ ID NO: 23). All measurements may be performed at 25° C. HBS-EP+ buffer (10 mM HEPES pH 7.4, 150 mM NaCl, 3 mM EDTA, 0.05% surfactant P20; #BR-1006-69) can be used as the running buffer and sample buffer. Mouse IgG1 anti-polyhistidine antibody (R&D systems, Mab050) may be immobilized on flow cells 1 to 4 of a CMS sensor chip at a level of 7000 response units (Rus) using an amine coupling kit to capture human c-Met-ECD-Fc-Flis. Human c-Met-ECD-Fc-Flis may be first injected to flow cell 2. An antibody, or antigen-binding fragment thereof, of the present invention may be initially injected at 50 nM to fully saturate the c-Met-ECD-Fc-Flis on the chip surface. C8-H241 may then be injected immediately. Binding response units may be used to calculate binding stoichiometry. To show that simultaneous binding is independent of the addition order of the two antibodies, binding order may be reversed or alternated several times in the course of the experiment.

In experiments performed essentially as described in this Example 3, each c-Met-ECD-Fc-Flis binds 1.1 of Antibody I and 0.8 of C8-H241 (human IgG4 subtype) anti-c-Met antibodies. For Antibody II, each c-Met-ECD-Fc-Flis binds 1.5 of Antibody II and 0.9 of C8-H241 (CAS #1365287-97-3) anti-c-Met antibodies. All combinations of order addition show that Antibodies I and II can bind to cMet-ECD-Fc-Flis in the presence of C8-H241. These data show that Antibodies I and II and mAb C8-H241 (human IgG4 subtype) can simultaneously bind human c-Met-ECD-Fc-Flis, indicating that Antibody I and Antibody II could be used to detect c-Met levels in patient samples while treatment with C8-H241 is on-going, without requiring a wash-out period.

FACS

An in vitro assay designed to measure cell surface c-Met receptor may be conducted to determine if the antibodies of the present invention are capable of staining human c-Met on the cell surface while C8-H241 is also bound. Fluorescence-activated cell sorting (FACS) analysis may be used to demonstrate that c-Met antibody C8-H241 and an antibody of the present invention bind simultaneously to cell surface c-Met.

C8-H241 c-Met antibody may be labeled with an Alexa Fluor 488 Monoclonal Antibody Labeling Kit (Molecular Probes, Eugene, Oreg., #A-20181). Human gastric tumor MKN45 cells (Japan Health Sciences Foundation, Health Science Research Resource Bank, #JCRB0254) may be cultured in RPMI-1640 (Invitrogen, #11835), 10% (v/v) FBS (Invitrogen, #10082); 2 mM L-glutamine (Invitrogen, #25030); 100 U/500 mL penicillin G, and 100 micrograms/500 mL streptomycin (Invitrogen, #15140). The MKN45 cells from a T75 flask may be dissociated with 5 mL of enzyme-free cell dissociation solution (Chemicon, #S-014-B). The cells may be collected into centrifuge tubes after being incubated for 5 minutes at room temperature, and washed once in culture medium followed by an additional wash in binding buffer (Dulbecco's phosphate buffered saline (DPBS) with 1% (w/v) BSA and 0.1% (w/v) sodium azide). 100 microliters of binding buffer containing 5 microgram/mL of the anti-c-Met antibody, or antigen-binding fragment thereof, of the invention may be added to the cells. The cells may be incubated for 30 minutes and then washed with 1 mL of binding buffer. 100 microliters of binding buffer containing 5 microgram/mL of Alexa Fluor 647 (Invitrogen, #A21236) labeled anti-mIgG may then be added and incubated for 30 minutes on ice. Then 10 microliters of 50 microgram/mL Alexa Fluor 488 labeled C8-H241 (final concentration of 5 microgram/mL) may be added to above staining solution and incubated for 30 minutes on ice. The cells may then be washed twice with binding buffer and resuspended in DPBS. The antibody binding to cell surface c-Met may be analyzed by FACS analysis with 20,000 events acquired for each sample.

In FACS experiments performed essentially as described in this Example 3, 98.68% of MKN45 cells are stained both by C8-H241 (CAS #1365287-97-3) and Antibody I. 98.64% of MKN45 cells are stained both by C8-H241 and Antibody II. These results indicate that Antibody I and Antibody II may be used to detect c-Met levels in patient samples while treatment with C8-H241 is on-going, without requiring a wash-out period.

EXAMPLE 4

Antibodies I and II Simultaneously Bind ECD of Human c-Met with MetMAb

To determine if an antibody, or antigen-binding fragment thereof, of the present invention can bind the ECD of human c-Met at the same time as MetMAb, a binding experiment may be performed using a surface plasmon resonance biosensor such as a BIAcore® 2000, BIAcore® 3000, or a BIAcore® T100 (GE Health Care, Piscataway, N.J.) according to methods known in the art. Except as noted, all reagents and materials may be purchased from BIAcore®. The c-Met-ECD with Fc and Flis tag (c-Met-ECD-Fc-Flis) can be expressed from CHO cells and purified for this analysis. All measurements may be performed at 25° C. HBS-EP+ buffer (10 mM HEPES pH 7.4, 150 mM NaCl, 3 mM EDTA, 0.05% surfactant P20; #BR-1006-69) can be used as the running buffer and sample buffer. Mouse IgG1 anti-polyhistidine antibody (R&D systems, Mab050) may be immobilized on flow cells 1 to 4 of a CMS sensor chip at a level of 6500 response units (Rus) using an amine coupling kit to capture human c-Met-ECD-Fc-Flis. Human c-Met-ECD-Fc-Flis may be first injected to flow cell 2. An antibody, or antigen-binding fragment thereof, of the present invention may be initially injected at 500 nM to fully saturate the c-Met-ECD-Fc-Flis on the chip surface. MetMAb may then be injected immediately. Binding response units may be used to calculate binding stoichiometry. To show that simultaneous binding is independent of the addition order of the two antibodies, binding order may be reversed or alternated several times in the course of the experiment.

In experiments performed essentially as described in this Example 4, each c-Met-ECD-Fc-Flis binds 1.5 of Antibody I and 1.3 of MetMAb, expressed in HEK 293 EBNA cells. For Antibody II, each c-Met-ECD-Fc-Flis binds 1.3 of Antibody II and 1.4 of MetMAb. All combinations of order addition show that Antibodies I and II can bind to cMet-ECD-Fc-Flis in the presence of MetMAb. These data show that Antibodies I, II, or MetMAb can simultaneously bind human c-Met-ECD-Fc-Flis. Furthermore, the data indicates that the epitopes of these anti-c-Met antibodies differ.

EXAMPLE 5

Diagnostic Assay for Circulating Tumor Cells in Blood Samples

The binding of antibodies, or antigen-binding fragments thereof, of the present invention to circulating tumor cells (CTCs) may be determined with use of the CellTracks® AutoPrep® System, and CellTracks Analyzer II® or Cell-Spotter® Analyzer. The detection of c-Met receptor expression in CTCs may use the open-channel (4th channel) of the analyzer. The open channel allows the use of fluorescent dye with excitation/emission wavelengths similar to either FITC (fluorescein) or PE (phycoerythrin). All reagents, unless otherwise specified, may be purchased from Veridex LLC (Raritan, N.J.).

R-phycoerithrin (R-PE) fluorescent dye and a thio conjugation chemistry kit (Dojindo, #LK26) may be used for conjugation with the antibodies, or antigen-binding fragments thereof, of the present invention. The R-PE conjugated antibody may be further purified using a Protein G affinity column for IgG prior to use for staining of c-Met in CTCs. R-PE-conjugated antibodies, or antigen-binding fragments thereof, of the present invention may be evaluated in the CTC assay for optimal concentration and PE channel acquisition time.

CTCs may be defined as cells that are positive for EpCAM (epithelial cell adhesion molecule), cytokeratin 8, 18, 19 and with nuclei (DAPI staining) and negative for CD45 (marker for leukocytes). CTCs may be enriched from a 7.5 ml patient blood sample by the addition of anti-EpCAM antibody-immuno-magnetic beads. After washing of these enriched CTCs, these cells may be immunofluorescently stained with antibodies against cytokeratin, nucleus and CD45. The R-PE-conjugated antibodies, or antigen-binding fragments thereof, of the present invention may be added to the assay procedure as part of the cell staining step. The antibody may be added to the Tumor Phenotyping Reagent Cup included in the Veridex CellSearch™ CXC kit, and then the CellTracks® AutoPrep® System may be used to analyze a patient sample. Alternatively, using the Veridex Mouse/Rat CellCapture™ CTC kit, the user may add the antibody concurrently with the DAPI and FITC stains manually. The CTCs contained in the sample cartridge within the MagNest® device may be visualized with the CellTracks Analyzer II® and images of the cells may be captured onto a computer, using software provided with this system.

In order to demonstrate the sensitivity of the CTC assay against different levels of c-Met expression, SKBR3, H441, SKOV3, MNK45, and SNUS cell lines may be chosen. SKBR3 cells (breast cancer cell line) do not express detectable levels of c-Met receptor. H441 cells (lung cancer cell line) express moderate levels of c-Met receptor. SKOV3 cells (ovarian cancer cell line) express low levels of c-Met receptor. MNK45 and SNUS, both gastric cancer cell lines, express high levels of c-Met receptor.

In experiments performed essentially as described in this Example 5, the optimal concentration of anti-c-Met antibody is found to be 0.1 microgram per test, and the optimal PE acquisition time was 0.005 to 0.007 seconds. Antibodies I and II are able to detect c-Met expression in cell lines expressing moderate and high levels of c-Met, while showing no staining in a cell line negative for c-Met.

Simultaneous Binding with C8-H241 and MetMAb

If a CTC assay is to be used in patients who are treated with c-Met targeted therapy, it is important to determine whether the therapeutic agent interferes with the diagnostic c-Met antibody. The interference of anti-c-Met therapeutic antibodies MetMAb or C8-H241 with the performance of the diagnostic test may be assessed by adding the therapeutic agent to cultured cells spiked into the test sample, and then staining for c-Met using R-PE-conjugated antibodies, or antigen-binding fragments thereof, of the present invention using the CTC assay as essentially described in this Example 5. MetMAb or C8-H241 antibodies may be added (0, 10, 30, and 90 µg/mL) to cultured cells diluted in Veridex Dilution Buffer containing 10% CellSave preservative. Test samples may be assayed for CTCs using the Veridex Mouse/Rat CellCapture™ CTC kit, following the instructions provided in the kit or procedures otherwise known in the art. Briefly, samples may be enriched for EpCam-positive cells, and then stained with FITC-anti-cytokeratins 8, 18, and 19, DAPI, and 0.1 µg R-PE-Antibody I or II. The stained cells may be placed in a sample cartridge placed within a MagNest® device, and the cartridge may be scanned on the CellTracks Analyzer IT®. Cell images may be captured, and cells identified as CTCs are assessed for c-Met staining in the PE channel.

C8-H241 (CAS #1365287-97-3) does not interfere with Antibody I or II (Tables 3 and 4). MetMAb, expressed in HEK 293 EBNA cells, may interfere slightly with Antibody I in cells with moderate c-Met expression, but not in cells with high levels of human c-Met. There is a slight reduction in % c-Met-positive H441 cells staining with PE-conjugated Antibody I, correlating with increasing dose of MetMAb (Table 5). This is not seen in the high MET expressing cell line, MKN45. MetMAb does not interfere with Antibody II (see, for example, Table 6). Visually, the image quality in the PE channel remained consistent with or without MetMAb, and a high percentage of H441 cells remained positive for c-Met at the highest MetMAb dose.

The results support the use of an antibody, or antigen-binding fragment thereof, of the present invention in a CTC assay as a patient selection and as a diagnostic antibody for therapeutic response in MetMAb or C8-H241 treated patients in clinical studies.

TABLE 3

Percentage of positively stained cells with R-PE-Antibody I in the CellTracks Analyzer II ® PE channel after incubation of cells with C8-H241

| Cell line | C8-H241 concentration (microgram/mL) | CTC count | % cells c-Met positive |
|---|---|---|---|
| H441 | 0 | 363 | 90.4 |
|  | 10 | 342 | 93.0 |

TABLE 3-continued

Percentage of positively stained cells with R-PE-Antibody I in the CellTracks Analyzer II ® PE channel after incubation of cells with C8-H241

| Cell line | C8-H241 concentration (microgram/mL) | CTC count | % cells c-Met positive |
|---|---|---|---|
|  | 30 | 384 | 94.5 |
|  | 90 | 347 | 94.5 |
| MKN45 | 0 | 151 | 98.7 |
|  | 10 | 142 | 97.9 |
|  | 30 | 160 | 96.3 |
|  | 90 | 119 | 99.2 |
| SKBR3 | 0 | 379 | 1.6 |
|  | 90 | 330 | 2.1 |

TABLE 4

Percentage of positively stained cells with R-PE-Antibody II in the CellTracks Analyzer II ® PE channel after incubation of cells with C8-H241

| Cell line | C8-H241 concentration (microgram/mL) | CTC count | % cells c-Met positive |
|---|---|---|---|
| H441 | 0 | 335 | 93.4 |
|  | 10 | 357 | 96.9 |
|  | 30 | 398 | 97.0 |
|  | 90 | 323 | 94.4 |
| MKN45 | 0 | 133 | 98.5 |
|  | 10 | 147 | 99.3 |
|  | 30 | 115 | 100 |
|  | 90 | 153 | 100 |
| SKBR3 | 0 | 277 | 3.3 |
|  | 90 | 377 | 0.8 |

TABLE 5

Percentage of positively stained cells with R-PE-Antibody I in the CellTracks Analyzer II ® PE channel after incubation of cells with MetMAb

| Cell line | MetMAb concentration count | CTC positive | % cells c-Met |
|---|---|---|---|
| H441 | 0 | 319 | 82.8 |
|  | 10 | 383 | 82.5 |
|  | 30 | 382 | 78.3 |
|  | 90 | 366 | 70.0 |
| MKN45 | 0 | 327 | 98.5 |
|  | 10 | 351 | 98.6 |
|  | 30 | 293 | 97.6 |
|  | 90 | 310 | 97.1 |
| SKBR3 | 0 | 376 | 1.1 |
|  | 90 | 345 | 0.3 |

TABLE 6

Percentage of positively stained cells with R-PE-Antibody II in the CellTracks Analyzer II ® PE channel after incubation of cells with MetMAb

| Cell line | MetMAb concentration count | CTC positive | % cells c-Met |
|---|---|---|---|
| H441 | 0 | 308 | 95.5 |
|  | 10 | 321 | 95.0 |
|  | 30 | 370 | 94.6 |
|  | 90 | 319 | 93.7 |

TABLE 6-continued

Percentage of positively stained cells with R-PE-Antibody II in the CellTracks Analyzer II ® PE channel after incubation of cells with MetMAb

| Cell line | MetMAb concentration count | CTC positive | % cells c-Met |
|---|---|---|---|
| MKN45 | 0 | 231 | 99.6 |
|  | 10 | 242 | 99.2 |
|  | 30 | 238 | 98.7 |
|  | 90 | 263 | 99.6 |
| SKBR3 | 0 | 350 | 2.3 |
|  | 90 | 305 | 0.3 |

EXAMPLE 6

Immunohistochemical (IHC) Assay for Human c-Met

An antibody, or antigen-binding fragment thereof, of the present invention may be used to detect human c-Met in normal or neoplastic human tissue that is formalin-fixed paraffin-embedded.

Briefly described, slides of human tissue or cancer cells may be prepared by baking at 60° C. for at least an hour or up to 16 hours, and then rehydrating and deparaffinizing in a series of xylene, ethanol, and water treatments on a linear stainer (Autostainer XL ST5010, Leica Microsystems). The extra-cellular domain epitope of Antibody II may be retrieved in the cells or tissues using Diva citrate antigen retrieval buffer (DV2004G1, Biocare Medical) in a high pressure decloaking chamber reaching 125° C. for 30 seconds.

The c-Met signal may be detected using the Leica Bond Refine Polymer kit (DS9800, Leica Microsystems) on the Leica Bond III automated slide stainer. Briefly, slides may be treated with Peroxide Block (3-4% hydrogen peroxide, component of DS9800, Leica Microsystems) for 5 minutes, PowerVision Super Block (PV6122, Leica Microsystems) for 10 minutes, Antibody II for 15 minutes, Post-Primary (rabbit anti-mouse IgG, component of DS9800, Leica Microsystems) for 8 minutes, Polymer (anti-rabbit poly-HRP-IgG, component of DS9800, Leica Microsystems) for 8 minutes, DAB Chromogen (from components of DS9800, Leica Microsystems) for 10 minutes, and hematoxylin counterstain (component of DS9800, Lecia Microsystems) for 5 minutes. Antibody II may be used at a concentration of 2 microgram/mL during the IHC protocol. Slides may be dehydrated from water to ethanol to xylene on a linear stainer (Autostainer XL ST5010, Leica Microsystems), and then coverslipped following routine procedures.

To determine if an antibody, or antigen-binding fragment thereof, of the present invention is selective for the ECD of human c-Met over the ECD of human RON, a pre-absorption/blocking experiment may be performed. The antibody, or antigen-binding fragment thereof, of the present invention at 2 microgram/mL may be incubated overnight with either c-Met-ECD-Fc-Flis (SEQ ID NO: 23) or the ECD of human RON (R&D Systems, #1947-MS-050) at 200× molar excess on a rotator at 4° C. After overnight incubation, the antibody, or antigen-binding fragment thereof, of the present invention may be tested against slides of human tissue or cancer cell lines as described above in Example 6.

In experiments performed essentially as described in this Example 6, the ECD of human c-MET blocks the immunoreactivity of Antibody II, while the ECD of human RON does not block the immunoreactivity of Antibody II staining. These findings support the selectivity of Antibody II to human c-MET over human RON.

For staining human tumor cell lines, 60 million cells may be harvested, formalin-fixed, and processed into histogel. The histogel cell pellets may be embedded into paraffin blocks, cored, and designed into a cell microarray that may be re-embedded in a paraffin block and then microtomed onto slides. These slides may be immunohistochemically stained and counterstained using the IHC assay protocol as described above in Example 6. MKN45 cells (human gastric carcinoma) and H441 cells (human lung adenocarcinoma) may be used as high c-MET expressers; U87MG cells (human glioblastoma-astrocytoma), H1299 (human non-small cell lung carcinoma), and Colo205 cells (human colon adenocarcinoma) may be used as intermediate expressers of c-MET; and SKBR3 (human breast carcinoma) and c-MET-transfected NIH 3T3 cells (mouse embryonic fibroblast cells transfected with human c-MET recombinant protein) may be used as low expressers of c-MET. RON-transfected NIH 3T3 cells and mock NIH 3T3 cells (mouse embryonic fibroblasts) are used as non-c-MET expressing negative controls.

In experiments performed essentially as described in this Example 6, Antibody II exhibits differential levels of immunostaining in various cell lines: strong cytoplasmic and membrane staining of 100% of the MKN45 and H441 cells with mostly negative nuclei; moderate to strong cytoplasmic and membrane staining of 100% of the U87MG, H1299, and Colo205 cells with mostly negative nuclei; and low to moderate cytoplasmic and membrane staining in 50% of the SKBR3 and in 90% of the c-MET-transfected NIH 3T3 cells with mostly negative nuclei. The mock and RON-transfected NIH 3T3 cells show only some faint cytoplasmic blush for c-Met staining and are considered negative.

For staining of human tumor tissues and normal human tissue, sections from tissue microarrays may be mounted on charged glass slides and stained with the IHC protocol as described above in Example 6. The results of the immunostaining by Antibody II may be scored by a pathologist. In experiments performed essentially as described in this Example 6, Antibody II was tested against non-small cell carcinomas of the lung (n=300), gastric carcinomas (n=61), cholangiocarcinomas (n=58), ovarian carcinomas (n=15), prostate carcinomas (n=256), and renal cell carcinomas of the kidney (n=140). A variety of immunohistochemical staining patterns (diffuse, focal, and variable) from one tumor type to another and also in different areas of the same tumor tissues are seen. Overall, Antibody II stains tumor cell membranes admixed with a variable component of cytoplasmic staining. The tumor cell nuclei are consistently stained negative, while taking up the hematoxylin counterstain. Similar to neoplastic tissues, the overall pattern of c-MET in normal human tissue (colon, kidney, uterus, liver, and lung) after testing with Antibody II is immunoreactivity that is cytoplasmic and membranous, while nuclei are consistently negative.

EXAMPLE 7

Second Immunohistochemical (IHC) Assay for Human c-Met

An antibody, or antigen-binding fragment thereof, of the present invention may be used to detect human c-Met in both commercially acquired formalin-fixed, paraffin embedded (FFPE) human biospecimen material in tissue microarray (TMA) format and whole sections of FFPE human biospecimen material.

Briefly described, slides of human tissue or cancer cells may be prepared by baking at 60° C. for at least 30 minutes or up to 2 hours to completely remove any residual water. Deparaffinization and extra-cellular domain epitope of Antibody II may be retrieved in the cells or tissues using EnVision™ FLEX Target Retrieval Solution, Low pH (K8005, Dako) in a Dako PT Link unit reaching 97° C. for 20 minutes.

The c-Met signal may be detected using the Dako EnVision™ FLEX+ Mouse (K8002, Dako) visualization system on the Dako Autostainer Link 48 automated slide stainer. Briefly, slides may be treated with the Peroxidase-Blocking Reagent (component of K8002, Dako) for 5 minutes, Antibody II for 15 minutes, Mouse (LINKER) reagent (signal amplifier, component of K8002, Dako) for 15 minutes, HRP polymer reagent (component of K8002, Dako) for 20 minutes, DAB chromogen/substrate working solution (from components of K8002, Dako) for 10 minutes, and hematoxylin counterstain (K8008, Dako) for 5 minutes. Antibody II may be used at a concentration of 2 µg/mL during the IHC protocol. Slides may be dehydrated from water, 95% ethanol, 100% ethanol, xylene, and then coverslipped following routine procedures.

For staining human tumor cell lines, 60 million cells may be harvested, formalin-fixed, and processed into histogel. The histogel cell pellets may be embedded into paraffin blocks, cored, and designed into a cell microarray that may be re-embedded in a paraffin block and then microtomed onto slides. These slides may be immunohistochemically stained and counterstained using the IHC assay protocol as described above in Example 7. RON-transfected NIH 3T3 cells and mock NIH 3T3 cells (mouse embryonic fibroblasts) are used as non-c-MET expressing negative controls.

In experiments performed essentially as described in this Example 7, Antibody II demonstrates selectivity over RON. In qualitative analysis by microscope, the mock and RON-transfected NIH 3T3 cells both show absent staining for RON with Antibody II and are considered negative, and quantitatively by digital image analysis, Antibody II is selective against RON as the pixel counts are compared for mock and RON-transfected NIH 3T3 cells (Table 7 and Table 8).

TABLE 7

Manual interpretation using brightfield microscope

| NIH3T3 Cell Line | EP1132Y antibody (Anti-RON) | Antibody II (Anti-cMET) |
|---|---|---|
| RON transfected | Staining intense | Staining absent |
| Mock (vector) transfected | Staining weak | Staining absent |

TABLE 8

Digital image analysis using Aperio Positive Pixel Count algorithm

| | NIH3T3 Cell Line | | | |
|---|---|---|---|---|
| | RON transfected | | Mock (vector) transfected | |
| Positive Pixel Count Category | EP1132Y antibody (Anti-RON) | Antibody II (Anti-cMET) | EP1132Y antibody (Anti-RON) | Antibody II (Anti-cMET) |
| Number of weak positive (Nwp) | 10247577 | 70901 | 986755 | 75739 |
| Number of positive (NP) | 10490504 | 5485 | 198671 | 12261 |
| Number of strong positive (Nsp) | 66915702 | 889 | 2055 | 4132 |
| Total number (NTotal) | 104754041 | 45098790 | 36341444 | 49071840 |
| Relative Positive Pixel Intensity Score | 221.45 | 0.19 | 3.83 | 0.23 |

In experiments performed essentially as described in this Example 7, Antibody II stains tumor cell membranes admixed with a variable component of cytoplasmic staining. The tumor cell nuclei are consistently stained negative, while taking up the hematoxylin counterstain. Similar to neoplastic tissues, the overall pattern of c-MET immunoreactivity in normal human tissue after testing with Antibody II is cytoplasmic and membranous, while nuclei are consistently negative. Archived, non-neoplastic human FFPE biospecimens, that can be stained when Antibody II include, but are not limited to, Type II pneumocytes (subset), vascular endothelium, basal cells of the prostatic and uterine glands, germinal center B-cells (centroblasts), cells of the stratum basle, cells of the collecting tubules (focally), hepatocytes, and focal glandular epithelium of the: endometerium, gastrointestinal tract, respiratory tract, and ovary. Archived, non-neoplastic FFPE human biospecimens not stained by Antibody II includes, but is not limited to, neuropil, resting T-cells, the superficial most layers of the stratum spinosum, luminal cells of the prostatic epithelium, and the molecular layer of the cerebellar cortex.

We claim:

1. An antibody, or antigen-binding fragment thereof, that specifically binds to the extracellular domain (ECD) of human c-Met (SEQ ID NO: 24), comprising a light chain variable region (LCVR) and a heavy chain variable region (HCVR), wherein the LCVR comprises the complementarity determining regions (CDRs) LCDR1, LCDR2, and LCDR3, and the HCVR comprises the CDRs HCDR1, HCDR2, and HCDR3, wherein the LCDR1 is the polypeptide of RASENIYSYLA (SEQ ID NO: 1), the LCDR2 is the polypeptide of VYNAKPLAE (SEQ ID NO: 2), the LCDR3 is the polypeptide of CQHHYGTPFT (SEQ ID NO: 3), the HCDR1 is the polypeptide of KASGYSFTSYWMY (SEQ ID NO: 4), the HCDR2 is the polypeptide of GFHPGNSGTNYNQKFKG (SEQ ID NO: 5) or GFHPRNSGTNYNQKFKG (SEQ ID NO: 6), and the HCDR3 is the polypeptide of TRGYYYDGSFTY (SEQ ID NO: 7).

2. The antibody, or antigen-binding fragment thereof, of claim 1, wherein the HCDR2 is the polypeptide of GFHPGNSGTNYNQKFKG (SEQ ID NO: 5).

3. The antibody, or antigen-binding fragment thereof, of claim 1, wherein the HCDR2 is the polypeptide of GFHPRNSGTNYNQKFKG (SEQ ID NO: 6).

4. The antibody, or antigen-binding fragment thereof, of claim 1, comprising an LCVR and an HCVR, wherein the LCVR is the polypeptide of SEQ ID NO: 8, and the HCVR is the polypeptide of SEQ ID NO: 9 or SEQ ID NO: 10.

5. The antibody, or antigen-binding fragment thereof, of claim 4, wherein the LCVR is the polypeptide of SEQ ID NO: 8, and the HCVR is the polypeptide of SEQ ID NO: 9.

6. The antibody, or antigen-binding fragment thereof, of claim 4, wherein the LCVR is the polypeptide of SEQ ID NO: 8, and the HCVR is the polypeptide of SEQ ID NO: 10.

7. The antibody, or antigen-binding fragment thereof, of claim 5, comprising a light chain (LC) and a heavy chain (HC), wherein the LC is the polypeptide of SEQ ID NO: 11, and the HC is the polypeptide of SEQ ID NO: 12.

8. The antibody, or antigen-binding fragment thereof, of claim 6, comprising a light chain (LC) and a heavy chain (HC), wherein the LC is the polypeptide of SEQ ID NO: 11, and the HC is the polypeptide of SEQ ID NO: 13.

9. The antibody of claim 7, comprising two light chains and two heavy chains, wherein each light chain is the polypeptide of SEQ ID NO: 11, and each heavy chain is the polypeptide of SEQ ID NO: 12.

10. The antibody of claim 8, comprising two light chains and two heavy chains, wherein each light chain is the polypeptide of SEQ ID NO: 11, and each heavy chain is the polypeptide of SEQ ID NO: 13.

11. A composition comprising an antibody, or antigen-binding fragment thereof, of claim 6, and an acceptable carrier, diluent, or excipient.

12. A kit comprising an antibody, or antigen-binding fragment thereof, of claim 6.

13. A method of detecting human c-Met expressed or overexpressed by a human cell, comprising:
    (a) contacting the cell in vitro with an antibody, or antigen-binding fragment thereof, of claim 6;
    (b) removing any unbound or non-specifically bound antibody, or antigen-binding fragment thereof; and
    (c) detecting and, optionally, quantifying the amount of antibody, or antigen-binding fragment thereof, which is specifically bound to the ECD of human c-Met (SEQ ID NO: 24).

14. The method of claim 13, wherein the human cell is formalin-fixed and paraffin-embedded.

15. The method of claim 13, wherein the detecting is performed by direct or indirect immunohistochemistry.

16. The method of claim 14, wherein the detecting is performed by direct or indirect immunohistochemistry.

17. A method of selecting a patient, having a tumor in which human c-Met is expressed or overexpressed, for treatment with an anti-c-Met therapeutic antibody or small molecule c-Met therapeutic compound, comprising:
    (a) contacting a sample of the tumor with an antibody, or antigen-binding fragment thereof, of claim 6;
    (b) removing any unbound or non-specifically bound antibody, or antigen-binding fragment thereof; and (c) detecting and, optionally, quantifying the amount of antibody, or antigen-binding fragment thereof, which is specifically bound to the ECD of human c-Met, wherein the presence of the antibody, or antigen-binding fragment thereof, specifically bound to the ECD of human c-Met identifies the patient as being appropriate for treatment with the anti-c-Met therapeutic antibody or small molecule c-Met therapeutic compound;

and wherein the anti-c-Met therapeutic agent is an antibody comprising two light chains and two heavy chains, wherein each of the light chains consists of the polypeptide of SEQ ID NO: 20 and each of the heavy chains consists of the polypeptide of SEQ ID NO: 22; or wherein the anti-c-Met agent is N-(3-Fluoro-4-(1-methyl-6-(1H-pyrazol-4-yl)-1H-indazol-5-yloxy)phenyl)-1-(4-fluorophenyl)-6-methyl-2-oxo-1,2-dihydropyridine-3-carboxamide or 6-(1-Methyl-1H-pyrazol-4-yl)-3-(2-methyl-2H-indazol-5-ylthio)-[1,2,4]triazolo[4,3-b]pyridazine.

18. The method of claim 17, wherein the human cell is formalin-fixed and paraffin-embedded.

19. The method of claim 17, wherein the detecting is performed by direct or indirect immunohistochemistry.

20. The method of claim 18, wherein the detecting is performed by direct or indirect immunohistochemistry.

21. A method of treating cancer, comprising:
(a) selecting a patient in need of treatment thereof, wherein the patient has a tumor in which human c-Met is expressed or overexpressed as determined by detecting human c-Met with an antibody, or antigen-binding fragment thereof, of claim 6; and
(b) treating the patient with an anti-c-Met therapeutic agent, wherein the anti-c-Met therapeutic agent is an antibody comprising two light chains and two heavy chains, wherein each of the light chains consists of the polypeptide of SEQ ID NO: 20 and each of the heavy chains consists of the polypeptide of SEQ ID NO: 22, or wherein the anti-c-Met agent is N-(3-Fluoro-4-(1-methyl-6-(1H-pyrazol-4-yl)-1H-indazol-5-yloxy)phenyl)-1-(4-fluorophenyl)-6-methyl-2-oxo-1,2-dihydropyridine-3-carboxamide or 6-(1-Methyl-1H-pyrazol-4-yl)-3-(2-methyl-2H-indazol-5-ylthio)-[1,2,4]triazolo[4,3-b]pyridazine.

22. The method of claim 21, wherein the human cell is formalin-fixed and paraffin-embedded.

23. The method of claim 21, wherein the detecting is performed by direct or indirect immunohistochemistry.

24. The method of claim 22, wherein the detecting is performed by direct or indirect immunohistochemistry.

* * * * *

SEQUENCE LISTING

```
<160> NUMBER OF SEQ ID NOS: 28

<210> SEQ ID NO 1
<211> LENGTH: 11
<212> TYPE: PRT
<213> ORGANISM: artificial sequence
<220> FEATURE:
<223> OTHER INFORMATION: synthetic construct

<400> SEQUENCE: 1

Arg Ala Ser Glu Asn Ile Tyr Ser Tyr Leu Ala
1               5                   10

<210> SEQ ID NO 2
<211> LENGTH: 9
<212> TYPE: PRT
<213> ORGANISM: artificial sequence
<220> FEATURE:
<223> OTHER INFORMATION: synthetic construct

<400> SEQUENCE: 2

Val Tyr Asn Ala Lys Pro Leu Ala Glu
1               5

<210> SEQ ID NO 3
<211> LENGTH: 10
<212> TYPE: PRT
<213> ORGANISM: artificial sequence
<220> FEATURE:
<223> OTHER INFORMATION: synthetic construct
```

```
<400> SEQUENCE: 3

Cys Gln His His Tyr Gly Thr Pro Phe Thr
1               5                   10

<210> SEQ ID NO 4
<211> LENGTH: 13
<212> TYPE: PRT
<213> ORGANISM: artificial sequence
<220> FEATURE:
<223> OTHER INFORMATION: synthetic construct

<400> SEQUENCE: 4

Lys Ala Ser Gly Tyr Ser Phe Thr Ser Tyr Trp Met Tyr
1               5                   10

<210> SEQ ID NO 5
<211> LENGTH: 17
<212> TYPE: PRT
<213> ORGANISM: artificial sequence
<220> FEATURE:
<223> OTHER INFORMATION: synthetic construct

<400> SEQUENCE: 5

Gly Phe His Pro Gly Asn Ser Gly Thr Asn Tyr Asn Gln Lys Phe Lys
1               5                   10                  15

Gly

<210> SEQ ID NO 6
<211> LENGTH: 17
<212> TYPE: PRT
<213> ORGANISM: artificial sequence
<220> FEATURE:
<223> OTHER INFORMATION: synthetic construct

<400> SEQUENCE: 6

Gly Phe His Pro Arg Asn Ser Gly Thr Asn Tyr Asn Gln Lys Phe Lys
1               5                   10                  15

Gly

<210> SEQ ID NO 7
<211> LENGTH: 12
<212> TYPE: PRT
<213> ORGANISM: artificial sequence
<220> FEATURE:
<223> OTHER INFORMATION: synthetic construct

<400> SEQUENCE: 7

Thr Arg Gly Tyr Tyr Tyr Asp Gly Ser Phe Thr Tyr
1               5                   10

<210> SEQ ID NO 8
<211> LENGTH: 107
<212> TYPE: PRT
<213> ORGANISM: artificial sequence
<220> FEATURE:
<223> OTHER INFORMATION: synthetic construct

<400> SEQUENCE: 8

Glu Ile Gln Met Thr Gln Ser Pro Ala Ser Leu Ser Ala Ser Val Gly
1               5                   10                  15

Glu Thr Val Thr Ile Thr Cys Arg Ala Ser Glu Asn Ile Tyr Ser Tyr
            20                  25                  30

Leu Ala Trp Tyr Gln Arg Lys Gln Gly Arg Ser Pro Gln Leu Leu Val
        35                  40                  45
```

Tyr Asn Ala Lys Pro Leu Ala Glu Gly Val Pro Ser Arg Phe Ser Gly
        50                  55                  60

Ser Gly Ser Gly Thr Gln Phe Ser Leu Lys Ile Asn Ser Leu Gln Pro
65                  70                  75                  80

Glu Asp Phe Gly Thr Tyr Tyr Cys Gln His His Tyr Gly Thr Pro Phe
                85                  90                  95

Thr Phe Gly Ser Gly Thr Arg Leu Glu Ile Lys
            100                 105

<210> SEQ ID NO 9
<211> LENGTH: 119
<212> TYPE: PRT
<213> ORGANISM: artificial sequence
<220> FEATURE:
<223> OTHER INFORMATION: synthetic construct

<400> SEQUENCE: 9

Glu Val Gln Leu Gln Gln Ser Gly Thr Val Leu Ala Arg Pro Gly Ala
1               5                   10                  15

Ser Val Lys Met Ser Cys Lys Ala Ser Gly Tyr Ser Phe Thr Ser Tyr
                20                  25                  30

Trp Met Tyr Trp Val Lys Gln Arg Pro Gly Gln Gly Leu Glu Trp Ile
            35                  40                  45

Gly Gly Phe His Pro Gly Asn Ser Gly Thr Asn Tyr Asn Gln Lys Phe
        50                  55                  60

Lys Gly Lys Ala Lys Leu Thr Ala Val Thr Ser Ala Ser Thr Ala Tyr
65                  70                  75                  80

Met Glu Leu Ser Ser Leu Thr Asn Glu Asp Ser Ala Val Tyr Tyr Cys
                85                  90                  95

Thr Arg Gly Tyr Tyr Tyr Asp Gly Ser Phe Thr Tyr Trp Gly Gln Gly
            100                 105                 110

Thr Leu Val Thr Val Ser Ala
        115

<210> SEQ ID NO 10
<211> LENGTH: 119
<212> TYPE: PRT
<213> ORGANISM: artificial sequence
<220> FEATURE:
<223> OTHER INFORMATION: synthetic construct

<400> SEQUENCE: 10

Glu Val Gln Leu Gln Gln Ser Gly Thr Val Leu Ala Arg Pro Gly Ala
1               5                   10                  15

Ser Val Lys Met Ser Cys Lys Ala Ser Gly Tyr Ser Phe Thr Ser Tyr
                20                  25                  30

Trp Met Tyr Trp Val Lys Gln Arg Pro Gly Gln Gly Leu Glu Trp Ile
            35                  40                  45

Gly Gly Phe His Pro Arg Asn Ser Gly Thr Asn Tyr Asn Gln Lys Phe
        50                  55                  60

Lys Gly Lys Ala Lys Leu Thr Ala Val Thr Ser Ala Ser Thr Ala Tyr
65                  70                  75                  80

Met Glu Leu Ser Ser Leu Thr Asn Glu Asp Ser Ala Val Tyr Tyr Cys
                85                  90                  95

Thr Arg Gly Tyr Tyr Tyr Asp Gly Ser Phe Thr Tyr Trp Gly Gln Gly
            100                 105                 110

Thr Leu Val Thr Val Ser Ala

<210> SEQ ID NO 11
<211> LENGTH: 214
<212> TYPE: PRT
<213> ORGANISM: artificial sequence
<220> FEATURE:
<223> OTHER INFORMATION: synthetic construct

<400> SEQUENCE: 11

Glu Ile Gln Met Thr Gln Ser Pro Ala Ser Leu Ser Ala Ser Val Gly
1               5                   10                  15

Glu Thr Val Thr Ile Thr Cys Arg Ala Ser Glu Asn Ile Tyr Ser Tyr
            20                  25                  30

Leu Ala Trp Tyr Gln Arg Lys Gln Gly Arg Ser Pro Gln Leu Leu Val
        35                  40                  45

Tyr Asn Ala Lys Pro Leu Ala Glu Gly Val Pro Ser Arg Phe Ser Gly
    50                  55                  60

Ser Gly Ser Gly Thr Gln Phe Ser Leu Lys Ile Asn Ser Leu Gln Pro
65                  70                  75                  80

Glu Asp Phe Gly Thr Tyr Tyr Cys Gln His His Tyr Gly Thr Pro Phe
                85                  90                  95

Thr Phe Gly Ser Gly Thr Arg Leu Glu Ile Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210

<210> SEQ ID NO 12
<211> LENGTH: 443
<212> TYPE: PRT
<213> ORGANISM: artificial sequence
<220> FEATURE:
<223> OTHER INFORMATION: synthetic construct

<400> SEQUENCE: 12

Glu Val Gln Leu Gln Gln Ser Gly Thr Val Leu Ala Arg Pro Gly Ala
1               5                   10                  15

Ser Val Lys Met Ser Cys Lys Ala Ser Gly Tyr Ser Phe Thr Ser Tyr
            20                  25                  30

Trp Met Tyr Trp Val Lys Gln Arg Pro Gly Gln Gly Leu Glu Trp Ile
        35                  40                  45

Gly Gly Phe His Pro Gly Asn Ser Gly Thr Asn Tyr Asn Gln Lys Phe
    50                  55                  60

Lys Gly Lys Ala Lys Leu Thr Ala Val Thr Ser Ala Ser Thr Ala Tyr
65                  70                  75                  80

```
Met Glu Leu Ser Ser Leu Thr Asn Glu Asp Ser Ala Val Tyr Tyr Cys
             85                  90                  95

Thr Arg Gly Tyr Tyr Asp Gly Ser Phe Thr Tyr Trp Gly Gln Gly
            100                 105                 110

Thr Leu Val Thr Val Ser Ala Ala Lys Thr Thr Pro Pro Ser Val Tyr
            115                 120                 125

Pro Leu Ala Pro Gly Ser Ala Ala Gln Thr Asn Ser Met Val Thr Leu
130                 135                 140

Gly Cys Leu Val Lys Gly Tyr Phe Pro Glu Pro Val Thr Val Thr Trp
145                 150                 155                 160

Asn Ser Gly Ser Leu Ser Ser Gly Val His Thr Phe Pro Ala Val Leu
            165                 170                 175

Gln Ser Asp Leu Tyr Thr Leu Ser Ser Val Thr Val Pro Ser Ser
            180                 185                 190

Thr Trp Pro Ser Glu Thr Val Thr Cys Asn Val Ala His Pro Ala Ser
            195                 200                 205

Ser Thr Lys Val Asp Lys Lys Ile Val Pro Arg Asp Cys Gly Cys Lys
            210                 215                 220

Pro Cys Ile Cys Thr Val Pro Glu Val Ser Ser Val Phe Ile Phe Pro
225                 230                 235                 240

Pro Lys Pro Lys Asp Val Leu Thr Ile Thr Leu Thr Pro Lys Val Thr
            245                 250                 255

Cys Val Val Val Asp Ile Ser Lys Asp Asp Pro Glu Val Gln Phe Ser
            260                 265                 270

Trp Phe Val Asp Asp Val Glu Val His Thr Ala Gln Thr Gln Pro Arg
            275                 280                 285

Glu Glu Gln Phe Asn Ser Thr Phe Arg Ser Val Ser Glu Leu Pro Ile
            290                 295                 300

Met His Gln Asp Trp Leu Asn Gly Lys Glu Phe Lys Cys Arg Val Asn
305                 310                 315                 320

Ser Ala Ala Phe Pro Ala Pro Ile Glu Lys Thr Ile Ser Lys Thr Lys
                325                 330                 335

Gly Arg Pro Lys Ala Pro Gln Val Tyr Thr Ile Pro Pro Lys Glu
            340                 345                 350

Gln Met Ala Lys Asp Lys Val Ser Leu Thr Cys Met Ile Thr Asp Phe
            355                 360                 365

Phe Pro Glu Asp Ile Thr Val Glu Trp Gln Trp Asn Gly Gln Pro Ala
370                 375                 380

Glu Asn Tyr Lys Asn Thr Gln Pro Ile Met Asp Thr Asp Gly Ser Tyr
385                 390                 395                 400

Phe Val Tyr Ser Lys Leu Asn Val Gln Lys Ser Asn Trp Glu Ala Gly
            405                 410                 415

Asn Thr Phe Thr Cys Ser Val Leu His Glu Gly Leu His Asn His His
            420                 425                 430

Thr Glu Lys Ser Leu Ser His Ser Pro Gly Lys
            435                 440
```

<210> SEQ ID NO 13
<211> LENGTH: 443
<212> TYPE: PRT
<213> ORGANISM: artificial sequence
<220> FEATURE:
<223> OTHER INFORMATION: synthetic construct

<400> SEQUENCE: 13

```
Glu Val Gln Leu Gln Gln Ser Gly Thr Val Leu Ala Arg Pro Gly Ala
1               5                   10                  15

Ser Val Lys Met Ser Cys Lys Ala Ser Gly Tyr Ser Phe Thr Ser Tyr
            20                  25                  30

Trp Met Tyr Trp Val Lys Gln Arg Pro Gly Gln Gly Leu Glu Trp Ile
        35                  40                  45

Gly Gly Phe His Pro Arg Asn Ser Gly Thr Asn Tyr Asn Gln Lys Phe
    50                  55                  60

Lys Gly Lys Ala Lys Leu Thr Ala Val Thr Ser Ala Ser Thr Ala Tyr
65                  70                  75                  80

Met Glu Leu Ser Ser Leu Thr Asn Glu Asp Ser Ala Val Tyr Tyr Cys
                85                  90                  95

Thr Arg Gly Tyr Tyr Tyr Asp Gly Ser Phe Thr Tyr Trp Gly Gln Gly
            100                 105                 110

Thr Leu Val Thr Val Ser Ala Ala Lys Thr Thr Pro Pro Ser Val Tyr
            115                 120                 125

Pro Leu Ala Pro Gly Ser Ala Ala Gln Thr Asn Ser Met Val Thr Leu
        130                 135                 140

Gly Cys Leu Val Lys Gly Tyr Phe Pro Glu Pro Val Thr Val Thr Trp
145                 150                 155                 160

Asn Ser Gly Ser Leu Ser Ser Gly Val His Thr Phe Pro Ala Val Leu
                165                 170                 175

Gln Ser Asp Leu Tyr Thr Leu Ser Ser Ser Val Thr Val Pro Ser Ser
            180                 185                 190

Thr Trp Pro Ser Glu Thr Val Thr Cys Asn Val Ala His Pro Ala Ser
        195                 200                 205

Ser Thr Lys Val Asp Lys Lys Ile Val Pro Arg Asp Cys Gly Cys Lys
    210                 215                 220

Pro Cys Ile Cys Thr Val Pro Glu Val Ser Ser Val Phe Ile Phe Pro
225                 230                 235                 240

Pro Lys Pro Lys Asp Val Leu Thr Ile Thr Leu Thr Pro Lys Val Thr
                245                 250                 255

Cys Val Val Val Asp Ile Ser Lys Asp Asp Pro Glu Val Gln Phe Ser
            260                 265                 270

Trp Phe Val Asp Asp Val Glu Val His Thr Ala Gln Thr Gln Pro Arg
        275                 280                 285

Glu Glu Gln Phe Asn Ser Thr Phe Arg Ser Val Ser Glu Leu Pro Ile
    290                 295                 300

Met His Gln Asp Trp Leu Asn Gly Lys Glu Phe Lys Cys Arg Val Asn
305                 310                 315                 320

Ser Ala Ala Phe Pro Ala Pro Ile Glu Lys Thr Ile Ser Lys Thr Lys
                325                 330                 335

Gly Arg Pro Lys Ala Pro Gln Val Tyr Thr Ile Pro Pro Lys Glu
            340                 345                 350

Gln Met Ala Lys Asp Lys Val Ser Leu Thr Cys Met Ile Thr Asp Phe
        355                 360                 365

Phe Pro Glu Asp Ile Thr Val Glu Trp Gln Trp Asn Gly Gln Pro Ala
    370                 375                 380

Glu Asn Tyr Lys Asn Thr Gln Pro Ile Met Asp Thr Asp Gly Ser Tyr
385                 390                 395                 400

Phe Val Tyr Ser Lys Leu Asn Val Gln Lys Ser Asn Trp Glu Ala Gly
                405                 410                 415

Asn Thr Phe Thr Cys Ser Val Leu His Glu Gly Leu His Asn His His
```

```
                420                 425                 430
Thr Glu Lys Ser Leu Ser His Ser Pro Gly Lys
        435                 440

<210> SEQ ID NO 14
<211> LENGTH: 321
<212> TYPE: DNA
<213> ORGANISM: artificial sequence
<220> FEATURE:
<223> OTHER INFORMATION: synthetic construct

<400> SEQUENCE: 14
gaaatccaga tgacccagtc tccagcctcc ctatctgcat ctgtgggaga aactgtcacc     60
atcacatgtc gagcaagtga gaatatttac agttatttag catggtatca gcggaaacag    120
ggaagatctc ctcagctcct ggtctataat gcaaaaccct tagcagaagg tgtgccatca    180
aggttcagtg gcagtggatc aggcacacag ttttctctga agatcaacag cctgcagcct    240
gaagattttg ggacttatta ctgtcaacat cattatggta ctccattcac gttcggctcg    300
gggaccagac tggaaataaa a                                              321

<210> SEQ ID NO 15
<211> LENGTH: 357
<212> TYPE: DNA
<213> ORGANISM: artificial sequence
<220> FEATURE:
<223> OTHER INFORMATION: synthetic construct

<400> SEQUENCE: 15
gaggttcagc tgcagcagtc tgggactgta ctggcaaggc ctggggcttc cgtgaagatg     60
tcctgcaagg cttctggcta cagctttacc agctactgga tgtactgggt aaaacagagg    120
cctggacagg gtctagaatg gattggtggt tttcatcctg aaatagtgg tactaactac     180 aaccagaagt tcaagggcaa ggccaaactg actgcagtca catccgccag tactgcctac    240
atggagctca gcagcctgac aaatgaagac tctgcggtct attactgtac aaggggttat    300
tactacgatg gttcgtttac ttactggggc caagggactc tggtcactgt ctctgca       357

<210> SEQ ID NO 16
<211> LENGTH: 357
<212> TYPE: DNA
<213> ORGANISM: artificial sequence
<220> FEATURE:
<223> OTHER INFORMATION: synthetic construct

<400> SEQUENCE: 16
gaggttcagc tgcagcagtc tgggactgta ctggcaaggc ctggggcttc cgtgaagatg     60
tcctgcaagg cttctggcta cagctttacc agctactgga tgtactgggt aaaacagagg    120
cctggacagg gtctagaatg gattggtggt tttcatcctc gtaatagtgg tactaactac    180
aaccagaagt tcaagggcaa ggccaaactg actgcagtca catccgccag tactgcctac    240
atggagctca gcagcctgac aaatgaagac tctgcggtct attactgtac aaggggttat    300
tactacgatg gttcgtttac ttactggggc caagggactc tggtcactgt ctctgca       357

<210> SEQ ID NO 17
<211> LENGTH: 642
<212> TYPE: DNA
<213> ORGANISM: artificial sequence
<220> FEATURE:
<223> OTHER INFORMATION: synthetic construct
```

<400> SEQUENCE: 17

```
gaaatccaga tgacccagtc tccagcctcc ctatctgcat ctgtgggaga aactgtcacc    60
atcacatgtc gagcaagtga gaatatttac agttatttag catggtatca gcggaaacag   120
ggaagatctc ctcagctcct ggtctataat gcaaaaccct tagcagaagg tgtgccatca   180
aggttcagtg gcagtggatc aggcacacag ttttctctga agatcaacag cctgcagcct   240
gaagattttg ggacttatta ctgtcaacat cattatggta ctccattcac gttcggctcg   300
gggaccagac tggaaataaa acgggctgat gcggcgccca ctgtatccat cttcccacca   360
tccagtgagc agttaacatc tggaggtgcc tcagtcgtgt gcttcttgaa caacttctac   420
cccaaagaca tcaatgtcaa gtggaagatt gatggcagtg aacgacaaaa tggcgtcctg   480
aacagttgga ctgatcagga cagcaaagac agcacctaca gcatgagcag cccctcacg    540
ttgaccaagg acgagtatga acgacataac agctatacct gtgaggccac tcacaagaca   600
tcaacttcac ccattgtcaa gagcttcaac aggaatgagt gt                      642
```

<210> SEQ ID NO 18
<211> LENGTH: 1329
<212> TYPE: DNA
<213> ORGANISM: artificial sequence
<220> FEATURE:
<223> OTHER INFORMATION: synthetic construct

<400> SEQUENCE: 18

```
gaggttcagc tgcagcagtc tgggactgta ctggcaaggc ctggggcttc cgtgaagatg    60
tcctgcaagg cttctggcta cagctttacc agctactgga tgtactgggt aaaacagagg   120
cctggacagg gtctagaatg gattggtggt tttcatcctg aaatagtgg tactaactac   180
aaccagaagt tcaagggcaa ggccaaactg actgcagtca catccgccag tactgcctac   240
atggagctca gcagcctgac aaatgaagac tctgcggtct attactgtac aaggggttat   300
tactacgatg gttcgtttac ttactggggc caagggactc tggtcactgt ctctgcagcc   360
aaaacgacac ccccatctgt ctatccgcta gcccctggat ctgccgccca gaccaacagc   420
atggtgaccc tgggctgtct ggtgaagggc tacttccctg agcctgtgac agtgacctgg   480
aacagcggct ctctgtctag cggcgtgcac acattccctg ccgtgctgca gagcgacctg   540
tacaccctga gcagcagcgt gaccgtgcct agcagcacat ggcctagcga gaccgtgaca   600
tgcaacgtgg cccacccctg ctcttctacc aaggtggaca agaagatcgt gcccagagac   660
tgcggctgca gccttgcat ctgcaccgtg cctgaggtga gcagcgtgtt catcttccca   720
cccaagccca aggacgtgct caccatcacc ctcaccccca aggtcacgtg tgttgtggta   780
gacatcagca aggatgatcc cgaggtccag ttcagctggt ttgtagatga tgtggaggtg   840
cacacagctc agacgcaacc ccgggaggag cagttcaaca gcactttccg ctcagtcagt   900
gaacttccca tcatgcacca ggactggctc aatggcaagg agttcaaatg cagggtcaac   960
agtgcagctt tccctgcccc catcgagaaa accatctcca aaaccaaagg cagaccgaag  1020
gctccacagg tgtacaccat tccacctccc aaggagcaga tggccaagga taaagtcagt  1080
ctgacctgca tgataacaga cttcttccct gaagacatta ctgtggagtg cagtggaat   1140
gggcagccag cggagaacta caagaacact cagcccatca tggacacaga tggctcttac  1200
ttcgtctaca gcaagctcaa tgtgcagaag agcaactggg aggcaggaaa tactttcacc  1260
tgctctgtgt tacatgaggg cctgcacaac caccatactg agaagagcct ctcccactct  1320
cctggtaaa                                                          1329
```

<210> SEQ ID NO 19
<211> LENGTH: 1329
<212> TYPE: DNA
<213> ORGANISM: artificial sequence
<220> FEATURE:
<223> OTHER INFORMATION: synthetic construct

<400> SEQUENCE: 19

```
gaggttcagc tgcagcagtc tgggactgta ctggcaaggc ctggggcttc cgtgaagatg    60
tcctgcaagg cttctggcta cagctttacc agctactgga tgtactgggt aaaacagagg   120
cctggacagg gtctagaatg gattggtggt tttcatcctc gtaatagtgg tactaactac   180
aaccagaagt tcaagggcaa ggccaaactg actgcagtca catccgccag tactgcctac   240
atggagctca gcagcctgac aaatgaagac tctgcggtct attactgtac aaggggttat   300
tactacgatg gttcgtttac ttactggggc caagggactc tggtcactgt ctctgcagcc   360
aaaacgacac cccatctgt ctatccgcta gcccctggat ctgccgccca gaccaacagc   420
atggtgaccc tgggctgtct ggtgaagggc tacttccctg agcctgtgac agtgacctgg   480
aacagcggct ctctgtctag cggcgtgcac acattccctg ccgtgctgca gagcgacctg   540
tacaccctga gcagcagcgt gaccgtgcct agcagcacat ggcctagcga gaccgtgaca   600
tgcaacgtgg cccacccctgc ctcttctacc aaggtggaca gaagatcgt gcccagagac   660
tgcggctgca agccttgcat ctgcaccgtg cctgaggtga gcagcgtgtt catcttccca   720
cccaagccca aggacgtgct caccatcacc ctcaccccca aggtcacgtg tgttgtggta   780
gacatcagca aggatgatcc cgaggtccag ttcagctggt ttgtagatga tgtggaggtg   840
cacacagctc agacgcaacc ccgggaggag cagttcaaca gcactttccg ctcagtcagt   900
gaacttccca tcatgcacca ggactggctc aatggcaagg agttcaaatg cagggtcaac   960
agtgcagctt ccctgccccc catcgagaaa accatctcca aaaccaaagg cagaccgaag  1020
gctccacagg tgtacaccat tccacctccc aaggagcaga tggccaagga taaagtcagt  1080
ctgacctgca tgataacaga cttcttccct gaagacatta ctgtggagtg cagtggaat   1140
gggcagccag cggagaacta caagaacact cagcccatca tggacacaga tggctcttac  1200
ttcgtctaca gcaagctcaa tgtgcagaag agcaactggg aggcaggaaa tactttcacc  1260
tgctctgtgt acatgagggg cctgcacaac caccatactg agaagagcct ctcccactct  1320
cctggtaaa                                                          1329
```

<210> SEQ ID NO 20
<211> LENGTH: 215
<212> TYPE: PRT
<213> ORGANISM: artificial sequence
<220> FEATURE:
<223> OTHER INFORMATION: synthetic construct

<400> SEQUENCE: 20

```
Asp Ile Gln Met Thr Gln Ser Pro Ser Ser Leu Ser Ala Ser Val Gly
1               5                   10                  15

Asp Arg Val Thr Ile Thr Cys Ser Val Ser Ser Val Ser Ser Ile
            20                  25                  30

Tyr Leu His Trp Tyr Gln Gln Lys Pro Gly Lys Ala Pro Lys Leu Leu
        35                  40                  45

Ile Tyr Ser Thr Ser Asn Leu Ala Ser Gly Val Pro Ser Arg Phe Ser
    50                  55                  60
```

```
Gly Ser Gly Ser Gly Thr Asp Phe Thr Leu Thr Ile Ser Ser Leu Gln
 65                  70                  75                  80

Pro Glu Asp Phe Ala Thr Tyr Tyr Cys Gln Val Tyr Ser Gly Tyr Pro
                 85                  90                  95

Leu Thr Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 21
<211> LENGTH: 440
<212> TYPE: PRT
<213> ORGANISM: artificial sequence
<220> FEATURE:
<223> OTHER INFORMATION: synthetic construct

<400> SEQUENCE: 21

Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Asp Tyr
             20                  25                  30

Tyr Met His Trp Val Arg Gln Ala Pro Gly Gln Gly Leu Glu Trp Met
         35                  40                  45

Gly Arg Val Asn Pro Asn Arg Gly Thr Thr Tyr Asn Gln Lys Phe
     50                  55                  60

Glu Gly Arg Val Thr Met Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Ala Arg Ala Asn Trp Leu Asp Tyr Trp Gly Gln Gly Thr Thr Val Thr
            100                 105                 110

Val Ser Ser Ala Ser Thr Lys Gly Pro Ser Val Phe Pro Leu Ala Pro
        115                 120                 125

Cys Ser Arg Ser Thr Ser Glu Ser Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Asn Phe Gly
            180                 185                 190

Thr Gln Thr Tyr Thr Cys Asn Val Asp His Lys Pro Ser Asn Thr Lys
        195                 200                 205
```

```
Val Asp Lys Thr Val Glu Arg Lys Cys Cys Val Glu Cys Pro Cys
    210             215                 220

Pro Ala Pro Pro Val Ala Gly Pro Ser Val Phe Leu Phe Pro Pro Lys
225             230                 235                 240

Pro Lys Asp Thr Leu Met Ile Ser Arg Thr Pro Glu Val Thr Cys Val
            245                 250                 255

Val Val Asp Val Ser His Glu Asp Pro Glu Val Gln Phe Asn Trp Tyr
            260                 265                 270

Val Asp Gly Met Glu Val His Asn Ala Lys Thr Lys Pro Arg Glu Glu
            275                 280                 285

Gln Phe Asn Ser Thr Phe Arg Val Val Ser Val Leu Thr Val Val His
    290                 295                 300

Gln Asp Trp Leu Asn Gly Lys Glu Tyr Lys Cys Lys Val Ser Asn Lys
305             310                 315                 320

Gly Leu Pro Ala Pro Ile Glu Lys Thr Ile Ser Lys Thr Lys Gly Gln
                325                 330                 335

Pro Arg Glu Pro Gln Val Tyr Thr Leu Pro Pro Ser Arg Glu Glu Met
            340                 345                 350

Thr Lys Asn Gln Val Ser Leu Thr Cys Leu Val Lys Gly Phe Tyr Pro
    355                 360                 365

Ser Asp Ile Ala Val Glu Trp Glu Ser Asn Gly Gln Pro Glu Asn Asn
370             375                 380

Tyr Lys Thr Thr Pro Pro Met Leu Asp Ser Asp Gly Ser Phe Phe Leu
385             390                 395                 400

Tyr Ser Lys Leu Thr Val Asp Lys Ser Arg Trp Gln Gln Gly Asn Val
                405                 410                 415

Phe Ser Cys Ser Val Met His Glu Ala Leu His Asn His Tyr Thr Gln
            420                 425                 430

Lys Ser Leu Ser Leu Ser Pro Gly
        435                 440

<210> SEQ ID NO 22
<211> LENGTH: 441
<212> TYPE: PRT
<213> ORGANISM: artificial sequence
<220> FEATURE:
<223> OTHER INFORMATION: synthetic construct

<400> SEQUENCE: 22

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Tyr Met His Trp Val Arg Gln Ala Pro Gly Gln Gly Leu Glu Trp Met
            35                  40                  45

Gly Arg Val Asn Pro Asn Arg Arg Gly Thr Thr Tyr Asn Gln Lys Phe
        50                  55                  60

Glu Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Ala Asn Trp Leu Asp Tyr Trp Gly Gln Gly Thr Thr Val Thr
            100                 105                 110

Val Ser Ser Ala Ser Thr Lys Gly Pro Ser Val Phe Pro Leu Ala Pro
        115                 120                 125
```

```
Cys Ser Arg Ser Thr Ser Glu Ser Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Lys Thr Tyr Thr Cys Asn Val Asp His Lys Pro Ser Asn Thr Lys
        195                 200                 205

Val Asp Lys Arg Val Glu Ser Lys Tyr Gly Pro Pro Cys Pro Pro Cys
210                 215                 220

Pro Ala Pro Glu Ala Ala Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser Gln Glu Asp Pro Glu Val Gln Phe Asn Trp
            260                 265                 270

Tyr Val Asp Gly Val Glu Val His Asn Ala Lys Thr Lys Pro Arg Glu
        275                 280                 285

Glu Gln Phe Asn Ser Thr Tyr Arg Val Val Ser Val Leu Thr Val Leu
    290                 295                 300

His Gln Asp Trp Leu Asn Gly Lys Glu Tyr Lys Cys Lys Val Ser Asn
305                 310                 315                 320

Lys Gly Leu Pro Ser Ser Ile Glu Lys Thr Ile Ser Lys Ala Lys Gly
                325                 330                 335

Gln Pro Arg Glu Pro Gln Val Tyr Thr Leu Pro Pro Ser Gln Glu Glu
            340                 345                 350

Met Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn
    370                 375                 380

Asn Tyr Lys Thr Thr Pro Pro Val Leu Asp Ser Asp Gly Ser Phe Phe
385                 390                 395                 400

Leu Tyr Ser Arg Leu Thr Val Asp Lys Ser Arg Trp Gln Glu Gly Asn
                405                 410                 415

Val Phe Ser Cys Ser Val Met His Glu Ala Leu His Asn His Tyr Thr
            420                 425                 430

Gln Lys Ser Leu Ser Leu Ser Leu Gly
        435                 440

<210> SEQ ID NO 23
<211> LENGTH: 1192
<212> TYPE: PRT
<213> ORGANISM: artificial sequence
<220> FEATURE:
<223> OTHER INFORMATION: synthetic construct

<400> SEQUENCE: 23

Met Lys Ala Pro Ala Val Leu Ala Pro Gly Ile Leu Val Leu Leu Phe
1               5                   10                  15

Thr Leu Val Gln Arg Ser Asn Gly Glu Cys Lys Glu Ala Leu Ala Lys
            20                  25                  30

Ser Glu Met Asn Val Asn Met Lys Tyr Gln Leu Pro Asn Phe Thr Ala
        35                  40                  45
```

```
Glu Thr Pro Ile Gln Asn Val Ile Leu His Glu His His Ile Phe Leu
 50              55                  60
Gly Ala Thr Asn Tyr Ile Tyr Val Leu Asn Glu Glu Asp Leu Gln Lys
 65                  70                  75                  80
Val Ala Glu Tyr Lys Thr Gly Pro Val Leu Glu His Pro Asp Cys Phe
                 85                  90                  95
Pro Cys Gln Asp Cys Ser Ser Lys Ala Asn Leu Ser Gly Gly Val Trp
            100                 105                 110
Lys Asp Asn Ile Asn Met Ala Leu Val Val Asp Thr Tyr Tyr Asp Asp
            115                 120                 125
Gln Leu Ile Ser Cys Gly Ser Val Asn Arg Gly Thr Cys Gln Arg His
130                 135                 140
Val Phe Pro His Asn His Thr Ala Asp Ile Gln Ser Glu Val His Cys
145                 150                 155                 160
Ile Phe Ser Pro Gln Ile Glu Pro Ser Gln Cys Pro Asp Cys Val
                165                 170                 175
Val Ser Ala Leu Gly Ala Lys Val Leu Ser Ser Val Lys Asp Arg Phe
            180                 185                 190
Ile Asn Phe Phe Val Gly Asn Thr Ile Asn Ser Ser Tyr Phe Pro Asp
            195                 200                 205
His Pro Leu His Ser Ile Ser Val Arg Arg Leu Lys Glu Thr Lys Asp
210                 215                 220
Gly Phe Met Phe Leu Thr Asp Gln Ser Tyr Ile Asp Val Leu Pro Glu
225                 230                 235                 240
Phe Arg Asp Ser Tyr Pro Ile Lys Tyr Val His Ala Phe Glu Ser Asn
                245                 250                 255
Asn Phe Ile Tyr Phe Leu Thr Val Gln Arg Glu Thr Leu Asp Ala Gln
            260                 265                 270
Thr Phe His Thr Arg Ile Ile Arg Phe Cys Ser Ile Asn Ser Gly Leu
            275                 280                 285
His Ser Tyr Met Glu Met Pro Leu Glu Cys Ile Leu Thr Glu Lys Arg
            290                 295                 300
Lys Lys Arg Ser Thr Lys Lys Glu Val Phe Asn Ile Leu Gln Ala Ala
305                 310                 315                 320
Tyr Val Ser Lys Pro Gly Ala Gln Leu Ala Arg Gln Ile Gly Ala Ser
                325                 330                 335
Leu Asn Asp Asp Ile Leu Phe Gly Val Phe Ala Gln Ser Lys Pro Asp
            340                 345                 350
Ser Ala Glu Pro Met Asp Arg Ser Ala Met Cys Ala Phe Pro Ile Lys
            355                 360                 365
Tyr Val Asn Asp Phe Phe Asn Lys Ile Val Asn Lys Asn Asn Val Arg
            370                 375                 380
Cys Leu Gln His Phe Tyr Gly Pro Asn His Glu His Cys Phe Asn Arg
385                 390                 395                 400
Thr Leu Leu Arg Asn Ser Ser Gly Cys Glu Ala Arg Arg Asp Glu Tyr
                405                 410                 415
Arg Thr Glu Phe Thr Thr Ala Leu Gln Arg Val Asp Leu Phe Met Gly
            420                 425                 430
Gln Phe Ser Glu Val Leu Leu Thr Ser Ile Ser Thr Phe Ile Lys Gly
            435                 440                 445
Asp Leu Thr Ile Ala Asn Leu Gly Thr Ser Glu Gly Arg Phe Met Gln
450                 455                 460
Val Val Val Ser Arg Ser Gly Pro Ser Thr Pro His Val Asn Phe Leu
```

-continued

```
        465                 470                 475                 480
Leu Asp Ser His Pro Val Ser Pro Glu Val Ile Val Glu His Thr Leu
                        485                 490                 495
Asn Gln Asn Gly Tyr Thr Leu Val Ile Thr Gly Lys Lys Ile Thr Lys
                500                 505                 510
Ile Pro Leu Asn Gly Leu Gly Cys Arg His Phe Gln Ser Cys Ser Gln
                515                 520                 525
Cys Leu Ser Ala Pro Pro Phe Val Gln Cys Gly Trp Cys His Asp Lys
530                 535                 540
Cys Val Arg Ser Glu Glu Cys Leu Ser Gly Thr Trp Thr Gln Gln Ile
545                 550                 555                 560
Cys Leu Pro Ala Ile Tyr Lys Val Phe Pro Asn Ser Ala Pro Leu Glu
                565                 570                 575
Gly Gly Thr Arg Leu Thr Ile Cys Gly Trp Asp Phe Gly Phe Arg Arg
                580                 585                 590
Asn Asn Lys Phe Asp Leu Lys Lys Thr Arg Val Leu Leu Gly Asn Glu
                595                 600                 605
Ser Cys Thr Leu Thr Leu Ser Glu Ser Thr Met Asn Thr Leu Lys Cys
        610                 615                 620
Thr Val Gly Pro Ala Met Asn Lys His Phe Asn Met Ser Ile Ile Ile
625                 630                 635                 640
Ser Asn Gly His Gly Thr Thr Gln Tyr Ser Thr Phe Ser Tyr Val Asp
                645                 650                 655
Pro Val Ile Thr Ser Ile Ser Pro Lys Tyr Gly Pro Met Ala Gly Gly
                660                 665                 670
Thr Leu Leu Thr Leu Thr Gly Asn Tyr Leu Asn Ser Gly Asn Ser Arg
                675                 680                 685
His Ile Ser Ile Gly Gly Lys Thr Cys Thr Leu Lys Ser Val Ser Asn
        690                 695                 700
Ser Ile Leu Glu Cys Tyr Thr Pro Ala Gln Thr Ile Ser Thr Glu Phe
705                 710                 715                 720
Ala Val Lys Leu Lys Ile Asp Leu Ala Asn Arg Glu Thr Ser Ile Phe
                725                 730                 735
Ser Tyr Arg Glu Asp Pro Ile Val Tyr Glu Ile His Pro Thr Lys Ser
                740                 745                 750
Phe Ile Ser Gly Gly Ser Thr Ile Thr Gly Val Gly Lys Asn Leu Asn
                755                 760                 765
Ser Val Ser Val Pro Arg Met Val Ile Asn Val His Glu Ala Gly Arg
770                 775                 780
Asn Phe Thr Val Ala Cys Gln His Arg Ser Asn Ser Glu Ile Ile Cys
785                 790                 795                 800
Cys Thr Thr Pro Ser Leu Gln Gln Leu Asn Leu Gln Leu Pro Leu Lys
                805                 810                 815
Thr Lys Ala Phe Phe Met Leu Asp Gly Ile Leu Ser Lys Tyr Phe Asp
                820                 825                 830
Leu Ile Tyr Val His Asn Pro Val Phe Lys Pro Phe Glu Lys Pro Val
                835                 840                 845
Met Ile Ser Met Gly Asn Glu Asn Val Leu Glu Ile Lys Gly Asn Asp
                850                 855                 860
Ile Asp Pro Glu Ala Val Lys Gly Glu Val Leu Lys Val Gly Asn Lys
865                 870                 875                 880
Ser Cys Glu Asn Ile His Leu His Ser Glu Ala Val Leu Cys Thr Val
                885                 890                 895
```

```
Pro Asn Asp Leu Leu Lys Leu Asn Ser Glu Leu Asn Ile Glu Trp Lys
            900                 905                 910

Gln Ala Ile Ser Ser Thr Val Leu Gly Lys Val Ile Val Gln Pro Asp
            915                 920                 925

Gln Asn Phe Thr Leu Glu Val Leu Phe Gln Gly Pro Asp Ile Glu Pro
            930                 935                 940

Lys Ser Cys Asp Lys Thr His Thr Cys Pro Pro Cys Pro Ala Pro Glu
945                 950                 955                 960

Leu Leu Gly Gly Pro Ser Val Phe Leu Phe Pro Pro Lys Pro Lys Asp
            965                 970                 975

Thr Leu Met Ile Ser Arg Thr Pro Glu Val Thr Cys Val Val Val Asp
            980                 985                 990

Val Ser His Glu Asp Pro Glu Val Lys Phe Asn Trp Tyr Val Asp Gly
            995                 1000                1005

Val Glu Val His Asn Ala Lys Thr Lys Pro Arg Glu Glu Gln Tyr
    1010                1015                1020

Asn Ser Thr Tyr Arg Val Val Ser Val Leu Thr Val Leu His Gln
    1025                1030                1035

Asp Trp Leu Asn Gly Lys Glu Tyr Lys Cys Lys Val Ser Asn Lys
    1040                1045                1050

Ala Leu Pro Ala Pro Ile Glu Lys Thr Ile Ser Lys Ala Lys Gly
    1055                1060                1065

Gln Pro Arg Glu Pro Gln Glu Tyr Thr Leu Pro Pro Ser Arg Glu
    1070                1075                1080

Glu Met Thr Lys Asn Gln Val Ser Leu Thr Cys Leu Val Lys Gly
    1085                1090                1095

Phe Tyr Pro Ser Asp Ile Ala Val Glu Trp Glu Ser Asn Gly Gln
    1100                1105                1110

Pro Glu Asn Asn Tyr Lys Thr Thr Pro Pro Val Leu Asp Ser Asp
    1115                1120                1125

Gly Ser Phe Phe Leu Tyr Ser Lys Leu Thr Val Asp Lys Ser Arg
    1130                1135                1140

Trp Gln Gln Gly Asn Val Phe Ser Cys Ser Val Met His Glu Ala
    1145                1150                1155

Leu His Asn His Tyr Thr Gln Lys Ser Leu Ser Leu Ser Pro Gly
    1160                1165                1170

Lys Arg Ile Asp Tyr Lys Asp Asp Asp Lys His Val His His
    1175                1180                1185

His His His His
    1190

<210> SEQ ID NO 24
<211> LENGTH: 908
<212> TYPE: PRT
<213> ORGANISM: homo sapien

<400> SEQUENCE: 24

Glu Cys Lys Glu Ala Leu Ala Lys Ser Glu Met Asn Val Asn Met Lys
1               5                   10                  15

Tyr Gln Leu Pro Asn Phe Thr Ala Glu Thr Pro Ile Gln Asn Val Ile
            20                  25                  30

Leu His Glu His His Ile Phe Leu Gly Ala Thr Asn Tyr Ile Tyr Val
            35                  40                  45

Leu Asn Glu Glu Asp Leu Gln Lys Val Ala Glu Tyr Lys Thr Gly Pro
```

-continued

```
                50                  55                  60
Val Leu Glu His Pro Asp Cys Phe Pro Cys Gln Asp Cys Ser Ser Lys
 65                  70                  75                  80

Ala Asn Leu Ser Gly Gly Val Trp Lys Asp Asn Ile Asn Met Ala Leu
                 85                  90                  95

Val Val Asp Thr Tyr Tyr Asp Asp Gln Leu Ile Ser Cys Gly Ser Val
            100                 105                 110

Asn Arg Gly Thr Cys Gln Arg His Val Phe Pro His Asn His Thr Ala
        115                 120                 125

Asp Ile Gln Ser Glu Val His Cys Ile Phe Ser Pro Gln Ile Glu Glu
    130                 135                 140

Pro Ser Gln Cys Pro Asp Cys Val Val Ser Ala Leu Gly Ala Lys Val
145                 150                 155                 160

Leu Ser Ser Val Lys Asp Arg Phe Ile Asn Phe Val Gly Asn Thr
                165                 170                 175

Ile Asn Ser Ser Tyr Phe Pro Asp His Pro Leu His Ser Ile Ser Val
            180                 185                 190

Arg Arg Leu Lys Glu Thr Lys Asp Gly Phe Met Phe Leu Thr Asp Gln
        195                 200                 205

Ser Tyr Ile Asp Val Leu Pro Glu Phe Arg Asp Ser Tyr Pro Ile Lys
    210                 215                 220

Tyr Val His Ala Phe Glu Ser Asn Asn Phe Ile Tyr Phe Leu Thr Val
225                 230                 235                 240

Gln Arg Glu Thr Leu Asp Ala Gln Thr Phe His Thr Arg Ile Ile Arg
                245                 250                 255

Phe Cys Ser Ile Asn Ser Gly Leu His Ser Tyr Met Glu Met Pro Leu
            260                 265                 270

Glu Cys Ile Leu Thr Glu Lys Arg Lys Arg Ser Thr Lys Lys Glu
        275                 280                 285

Val Phe Asn Ile Leu Gln Ala Ala Tyr Val Ser Lys Pro Gly Ala Gln
    290                 295                 300

Leu Ala Arg Gln Ile Gly Ala Ser Leu Asn Asp Asp Ile Leu Phe Gly
305                 310                 315                 320

Val Phe Ala Gln Ser Lys Pro Asp Ser Ala Glu Pro Met Asp Arg Ser
                325                 330                 335

Ala Met Cys Ala Phe Pro Ile Lys Tyr Val Asn Asp Phe Phe Asn Lys
            340                 345                 350

Ile Val Asn Lys Asn Asn Val Arg Cys Leu Gln His Phe Tyr Gly Pro
        355                 360                 365

Asn His Glu His Cys Phe Asn Arg Thr Leu Leu Arg Asn Ser Ser Gly
    370                 375                 380

Cys Glu Ala Arg Arg Asp Glu Tyr Arg Thr Glu Phe Thr Thr Ala Leu
385                 390                 395                 400

Gln Arg Val Asp Leu Phe Met Gly Gln Phe Ser Glu Val Leu Leu Thr
                405                 410                 415

Ser Ile Ser Thr Phe Ile Lys Gly Asp Leu Thr Ile Ala Asn Leu Gly
            420                 425                 430

Thr Ser Glu Gly Arg Phe Met Gln Val Val Val Ser Arg Ser Gly Pro
        435                 440                 445

Ser Thr Pro His Val Asn Phe Leu Leu Asp Ser His Pro Val Ser Pro
    450                 455                 460

Glu Val Ile Val Glu His Thr Leu Asn Gln Asn Gly Tyr Thr Leu Val
465                 470                 475                 480
```

```
Ile Thr Gly Lys Lys Ile Thr Lys Ile Pro Leu Asn Gly Leu Gly Cys
            485                 490                 495

Arg His Phe Gln Ser Cys Ser Gln Cys Leu Ser Ala Pro Pro Phe Val
            500                 505                 510

Gln Cys Gly Trp Cys His Asp Lys Cys Val Arg Ser Glu Glu Cys Leu
            515                 520                 525

Ser Gly Thr Trp Thr Gln Gln Ile Cys Leu Pro Ala Ile Tyr Lys Val
    530                 535                 540

Phe Pro Asn Ser Ala Pro Leu Glu Gly Gly Thr Arg Leu Thr Ile Cys
545                 550                 555                 560

Gly Trp Asp Phe Gly Phe Arg Arg Asn Asn Lys Phe Asp Leu Lys Lys
            565                 570                 575

Thr Arg Val Leu Leu Gly Asn Glu Ser Cys Thr Leu Thr Leu Ser Glu
            580                 585                 590

Ser Thr Met Asn Thr Leu Lys Cys Thr Val Gly Pro Ala Met Asn Lys
    595                 600                 605

His Phe Asn Met Ser Ile Ile Ile Ser Asn Gly His Gly Thr Thr Gln
    610                 615                 620

Tyr Ser Thr Phe Ser Tyr Val Asp Pro Val Ile Thr Ser Ile Ser Pro
625                 630                 635                 640

Lys Tyr Gly Pro Met Ala Gly Gly Thr Leu Leu Thr Leu Thr Gly Asn
            645                 650                 655

Tyr Leu Asn Ser Gly Asn Ser Arg His Ile Ser Ile Gly Gly Lys Thr
            660                 665                 670

Cys Thr Leu Lys Ser Val Ser Asn Ser Ile Leu Glu Cys Tyr Thr Pro
            675                 680                 685

Ala Gln Thr Ile Ser Thr Glu Phe Ala Val Lys Leu Lys Ile Asp Leu
    690                 695                 700

Ala Asn Arg Glu Thr Ser Ile Phe Ser Tyr Arg Glu Asp Pro Ile Val
705                 710                 715                 720

Tyr Glu Ile His Pro Thr Lys Ser Phe Ile Ser Gly Gly Ser Thr Ile
            725                 730                 735

Thr Gly Val Gly Lys Asn Leu Asn Ser Val Ser Val Pro Arg Met Val
            740                 745                 750

Ile Asn Val His Glu Ala Gly Arg Asn Phe Thr Val Ala Cys Gln His
            755                 760                 765

Arg Ser Asn Ser Glu Ile Ile Cys Cys Thr Thr Pro Ser Leu Gln Gln
    770                 775                 780

Leu Asn Leu Gln Leu Pro Leu Lys Thr Lys Ala Phe Phe Met Leu Asp
785                 790                 795                 800

Gly Ile Leu Ser Lys Tyr Phe Asp Leu Ile Tyr Val His Asn Pro Val
            805                 810                 815

Phe Lys Pro Phe Glu Lys Pro Val Met Ile Ser Met Gly Asn Glu Asn
            820                 825                 830

Val Leu Glu Ile Lys Gly Asn Asp Ile Asp Pro Glu Ala Val Lys Gly
            835                 840                 845

Glu Val Leu Lys Val Gly Asn Lys Ser Cys Glu Asn Ile His Leu His
    850                 855                 860

Ser Glu Ala Val Leu Cys Thr Val Pro Asn Asp Leu Leu Lys Leu Asn
865                 870                 875                 880

Ser Glu Leu Asn Ile Glu Trp Lys Gln Ala Ile Ser Ser Thr Val Leu
            885                 890                 895
```

```
Gly Lys Val Ile Val Gln Pro Asp Gln Asn Phe Thr
            900                 905
```

<210> SEQ ID NO 25
<211> LENGTH: 283
<212> TYPE: PRT
<213> ORGANISM: homo sapien

<400> SEQUENCE: 25

```
Glu Cys Lys Glu Ala Leu Ala Lys Ser Glu Met Asn Val Asn Met Lys
 1               5                  10                  15

Tyr Gln Leu Pro Asn Phe Thr Ala Glu Thr Pro Ile Gln Asn Val Ile
            20                  25                  30

Leu His Glu His His Ile Phe Leu Gly Ala Thr Asn Tyr Ile Tyr Val
        35                  40                  45

Leu Asn Glu Glu Asp Leu Gln Lys Val Ala Glu Tyr Lys Thr Gly Pro
    50                  55                  60

Val Leu Glu His Pro Asp Cys Phe Pro Cys Gln Asp Cys Ser Ser Lys
65                  70                  75                  80

Ala Asn Leu Ser Gly Gly Val Trp Lys Asp Asn Ile Asn Met Ala Leu
                85                  90                  95

Val Val Asp Thr Tyr Tyr Asp Asp Gln Leu Ile Ser Cys Gly Ser Val
            100                 105                 110

Asn Arg Gly Thr Cys Gln Arg His Val Phe Pro His Asn His Thr Ala
        115                 120                 125

Asp Ile Gln Ser Glu Val His Cys Ile Phe Ser Pro Gln Ile Glu Glu
    130                 135                 140

Pro Ser Gln Cys Pro Asp Cys Val Val Ser Ala Leu Gly Ala Lys Val
145                 150                 155                 160

Leu Ser Ser Val Lys Asp Arg Phe Ile Asn Phe Val Gly Asn Thr
                165                 170                 175

Ile Asn Ser Ser Tyr Phe Pro Asp His Pro Leu His Ser Ile Ser Val
            180                 185                 190

Arg Arg Leu Lys Glu Thr Lys Asp Gly Phe Met Phe Leu Thr Asp Gln
        195                 200                 205

Ser Tyr Ile Asp Val Leu Pro Glu Phe Arg Asp Ser Tyr Pro Ile Lys
    210                 215                 220

Tyr Val His Ala Phe Glu Ser Asn Asn Phe Ile Tyr Phe Leu Thr Val
225                 230                 235                 240

Gln Arg Glu Thr Leu Asp Ala Gln Thr Phe His Thr Arg Ile Ile Arg
                245                 250                 255

Phe Cys Ser Ile Asn Ser Gly Leu His Ser Tyr Met Glu Met Pro Leu
            260                 265                 270

Glu Cys Ile Leu Thr Glu Lys Arg Lys Lys Arg
        275                 280
```

<210> SEQ ID NO 26
<211> LENGTH: 212
<212> TYPE: PRT
<213> ORGANISM: homo sapien

<400> SEQUENCE: 26

```
Ser Thr Lys Lys Glu Val Phe Asn Ile Leu Gln Ala Ala Tyr Val Ser
 1               5                  10                  15

Lys Pro Gly Ala Gln Leu Ala Arg Gln Ile Gly Ala Ser Leu Asn Asp
            20                  25                  30
```

```
Asp Ile Leu Phe Gly Val Phe Ala Gln Ser Lys Pro Asp Ser Ala Glu
         35                  40                  45

Pro Met Asp Arg Ser Ala Met Cys Ala Phe Pro Ile Lys Tyr Val Asn
 50                  55                  60

Asp Phe Phe Asn Lys Ile Val Asn Lys Asn Val Arg Cys Leu Gln
 65                  70                  75                  80

His Phe Tyr Gly Pro Asn His Glu His Cys Phe Asn Arg Thr Leu Leu
                 85                  90                  95

Arg Asn Ser Ser Gly Cys Glu Ala Arg Arg Asp Glu Tyr Arg Thr Glu
                100                 105                 110

Phe Thr Thr Ala Leu Gln Arg Val Asp Leu Phe Met Gly Gln Phe Ser
            115                 120                 125

Glu Val Leu Leu Thr Ser Ile Ser Thr Phe Ile Lys Gly Asp Leu Thr
        130                 135                 140

Ile Ala Asn Leu Gly Thr Ser Glu Gly Arg Phe Met Gln Val Val Val
145                 150                 155                 160

Ser Arg Ser Gly Pro Ser Thr Pro His Val Asn Phe Leu Leu Asp Ser
                165                 170                 175

His Pro Val Ser Pro Glu Val Ile Val Glu His Thr Leu Asn Gln Asn
            180                 185                 190

Gly Tyr Thr Leu Val Ile Thr Gly Lys Lys Ile Thr Lys Ile Pro Leu
        195                 200                 205

Asn Gly Leu Gly
        210

<210> SEQ ID NO 27
<211> LENGTH: 227
<212> TYPE: PRT
<213> ORGANISM: artificial sequence
<220> FEATURE:
<223> OTHER INFORMATION: synthetic construct

<400> SEQUENCE: 27

Asp Lys Thr His Thr Cys Pro Pro Cys Pro Ala Pro Glu Leu Leu Gly
 1               5                  10                  15

Gly Pro Ser Val Phe Leu Phe Pro Pro Lys Pro Lys Asp Thr Leu Met
             20                  25                  30

Ile Ser Arg Thr Pro Glu Val Thr Cys Val Val Val Asp Val Ser His
         35                  40                  45

Glu Asp Pro Glu Val Lys Phe Asn Trp Tyr Val Asp Gly Val Glu Val
 50                  55                  60

His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
                 85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175
```

```
Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 28
<211> LENGTH: 449
<212> TYPE: PRT
<213> ORGANISM: artificial sequence
<220> FEATURE:
<223> OTHER INFORMATION: synthetic construct

<400> SEQUENCE: 28

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Ser Tyr
            20                  25                  30

Trp Leu His Trp Val Arg Gln Ala Pro Gly Lys Gly Leu Glu Trp Val
        35                  40                  45

Gly Met Ile Asp Pro Ser Asn Ser Asp Thr Arg Phe Asn Pro Asn Phe
    50                  55                  60

Lys Asp Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Thr Tyr Arg Ser Tyr Val Thr Pro Leu Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300
```

```
Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Glu Glu Met Thr Lys Asn Gln Val Ser Leu Ser
            355                 360                 365

Cys Ala Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Val Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
            435                 440                 445

Lys
```